(12) United States Patent
Sánchez García et al.

(10) Patent No.: US 11,930,808 B2
(45) Date of Patent: Mar. 19, 2024

(54) METHOD FOR OBTAINING AN ENRICHED POPULATION OF FUNCTIONAL MESENCHYMAL STEM CELLS, CELLS OBTAINED THEREOF AND COMPOSITIONS AND COMPRISING THE SAME

(71) Applicants: CITOSPIN, S.L., Valladolid (ES); UNIVERSIDAD DE VALLADOLID, Valladolid (ES)

(72) Inventors: Ana Sánchez García, Valladolid (ES); Francisco Javier García-Sancho Martín, Valladolid (ES); Verónica García Díaz, Valladolid (ES); Mercedes Alberca Zaballos, Valladolid (ES); Sandra Güemes Gutiérrez, Valladolid (ES)

(73) Assignees: UNIVERSIDAD DE VALLADOLID, Valladolid (ES); CITOSPIN, S.L., Valladolid (ES)

( * ) Notice: Subject to any disclaimer, the term of this patent is extended or adjusted under 35 U.S.C. 154(b) by 78 days.

(21) Appl. No.: 17/276,340

(22) PCT Filed: Sep. 18, 2019

(86) PCT No.: PCT/EP2019/074991
§ 371 (c)(1),
(2) Date: Mar. 15, 2021

(87) PCT Pub. No.: WO2020/058324
PCT Pub. Date: Mar. 26, 2020

(65) Prior Publication Data
US 2021/0321606 A1    Oct. 21, 2021

(30) Foreign Application Priority Data
Sep. 20, 2018   (EP) .................................... 18382679

(51) Int. Cl.
*A01N 1/02* (2006.01)
*A61K 35/28* (2015.01)
*C12N 5/0775* (2010.01)

(52) U.S. Cl.
CPC ......... *A01N 1/0221* (2013.01); *A01N 1/0226* (2013.01); *A61K 35/28* (2013.01); *C12N 5/0663* (2013.01)

(58) Field of Classification Search
CPC ..... A01N 1/0226; A61K 35/28; C12N 5/0663
See application file for complete search history.

(56) References Cited

U.S. PATENT DOCUMENTS 9,265,795 B2   2/2016   Hope et al.
2018/0325957 A1   11/2018   Kastrup et al.

FOREIGN PATENT DOCUMENTS

| EP | 2229436 | 8/2017 | |
| WO | 2010/064054 A1 | 6/2010 | |
| WO | WO 2010/064054 | 6/2010 | |
| WO | 2017/068140 A1 | 4/2017 | |
| WO | WO-2017068140 A1 * | 4/2017 | ........... A61K 9/0019 |
| WO | WO 2018/033911 | 2/2018 | |

OTHER PUBLICATIONS

Yang et al. Phenotypic and Functional Characterization of Long-Term Cryopreserved Human Adipose-derived Stem Cells 2017 Scientific Reports | 5 : 9596 (Year: 2017).*
Soleimani et al. A protocol for isolation and culture of mesenchymal stem cells from mouse bone marrow 2006 Nature Protocols vol. 4 (1): 102-106 (Year: 2006).*
Dontchos et al. Optimizing CO2 Normalizes pH and Enhances Chondrocyte Viability during Cold Storage 2008 J Orthop Res 26: 643-650 (Year: 2008).*
Ringwald et al. The New Generation of Platelet Additive Solution for Storage at 22° C.: Development and Current Experience vol. 20 (2): 158-164 (Year: 2006).*
Harb et al. Lactated Ringer-based storage solutions are equally well suited for the storage of fresh osteochondral allografts as cell culture medium-based storage solutions Injury, Int. J. Care Injured 48 (2017) 1302-1308 (Year: 2017).*
Jang et al. Cryopreservation and its clinical applications integr med res 6 ( 2017) 12-18 (Year: 2017).*
Backhach et al. The cryopreservation of composite tissues Principles and recent advancement on cryopreservation of different type of tissues 2009 Organogenesis 5:3, 119-126 (Year: 2009).*
Dominici et al. Minimal criteria for defining multipotent mesenchymal stromal cells. The International Society for Cellular Therapy position statement Cytotherapy (2006) vol. 8, No. 4, 315-317 (Year: 2006).*
Mata-Campuzano et al.Post-thawing quality and incubation resilience of cryopreserved ram spermatozoa are affected by antioxidant supplementation and choice of extender Theriogenology 83 (2015) 520-528) (Year: 2015).*
Mitchell et al., Cryopreservation of equine mesenchymal stem cells in 95% autologous serum and 5% DMSO does not alter post-thaw growth or morphology in vitro compared to fetal bovine serum or allogeneic serum at 20 or 95% and DMSO at 10 or 5%, Stem Cell Research & Therapy, 6(231): 1-12. (Year: 2015).*

(Continued)

*Primary Examiner* — Laura Schuberg
*Assistant Examiner* — Joseph Paul Miano
(74) *Attorney, Agent, or Firm* — Casimir Jones, SC; Tristan A. Fuierer

(57) ABSTRACT

A method to obtain a composition comprising an enriched population of functional mesenchymal stem cells for hypothermic transport and local administration of said enriched population of functional mesenchymal stem cells in therapy. Finally also described is the use of said enriched population of functional mesenchymal stem cells, and compositions comprising them, obtained by the described method, in autologous or allogeneic treatment of diseases susceptible to mesenchymal stem cell therapy, either by local or systemic treatments, and more particularly in the treatment of osteoarticular diseases such as degenerative disc disease, osteoarthritis, and bone repair; in lupus erythematosus, graft-versus-host disease, and other autoimmune diseases; in peripheral vascular insufficiency and other cardiovascular diseases.

14 Claims, 4 Drawing Sheets

(56) References Cited

OTHER PUBLICATIONS

Meuleman et al., Human marrow mesenchymal stem cell culture: serum-free medium allows better expansion than classical alpha-MEM medium, European Journal of Haematology, 76: 309-316. (Year: 2006).*
Nikolaev et al., The sensitivity of human mesenchymal stem cells to vibration and cold storage conditions representative of cold transportation, Journal of the Royal Society Interface, 9: 2503-2515. (Year: 2012).*
Hubel, Parameters of cell freezing: implications for the cryopreservation of stem cells, Transfusion Medicine Review, 11(3): 224-233. (Year: 1997).*
Czubak et al. Vitamin C and trolox decrease oxidative stress and hemolysis in cold-stored human red blood cells, Redox Report, 22 (6): 445-450. (Year: 2017).*
Dhansekaran et al., Unravelling the retention of proliferation and differentiation potency in extensive culture of human sub-cutaneous fat-derived mesenchymal stem cells in different media, Cell Proliferation, 45: 516-526. (Year: 2012).*
Monguió-Torajada et al., Mesenchymal stem cells induce expression of CD73 in human monocytes in vitro and in a swine model of myocardial infarction in vivo, Frontiers in Immunology, 8(1577): 1-13. (Year: 2017).*
Yong et al., Cryopreservation of human mesenchymal stem cells for clinical applications: current methods and challenges, 13(4): 231-239. (Year: 2015).*
International Search Report, dated Jan. 20, 2020, PCT/EP2019/074991.
Marquez-Curtizs, Leah A et al., "Mesenchymal stromal cells derived from various tissues: Biological, clinical and cryopreservation aspects," Cryobiology, Academic Press Inc, US vol. 71, No. 2, Jul. 14, 2015, 181-197, XP029278225.
Wei Duan et al., "Adult multipotent stromal cell cryopreservation: Pluses and pitfalls," Veterinary Surgery, vol. 47, No. 1, Oct. 12, 2017, 19-29, XP055545338.
Yuan, ZhengQiang et al., "Cryopreservation of human mesenchymal stromal cells expressing TRAIL for human anti-cancer therapy," Cytotherapy, vol. 18, No. 7, Jul. 1, 2016, 860-869, XP002774967.
Hugo Alves et al., "Effect of Antioxidant Supplementation on the Total Yield, Oxidative Stress Levels, and Multipotency of Bone Marrow-Derived human Mesenchymal Stromal cells," Tissue Engineering Part A, vol. 19, No. 7-8. Apr. 1, 2013, 928-937, XP055545351.
Lluis Orozco et al, "Treatment of Knee Osteoarthritis With Autologous Mesenchymal Stem Cells: A Pilot Study," Transplantation, vol. 95, No. 12, Jun. 1, 2013, 1535-1541, XP055488466.
Ringwald et al., "The New Generation of Platelet Additive Solution for Storage at 22° C.: Development and Current Experience," 2006, Transfusion Med Rev, vol. 20, No. 2, 158-164.
Dominici et al., "Minimal criteria for defining multipotent mesenchymal stromal cells. The International Society for Cellular Therapy position statement," Cytotherapy, 2006, vol. 8, No. 4, 315-317.
Wuchter et al, "Standardization of Good Manufacturing Practice—compliant production of bone marrow—derived human mesenchymal stromal cells for immunotherapeutic applications," Cytotherapy, 2015, 17:128-139.
Orozco et al., "Intervertebral Disc Repair by Autologous Mesenchymal Bone Marrow Cells: A Pilot Study," Transplantation, 2011, 92:822-828.
Vega et al., "Treatment of Knee Osteoarthritis With Allogeneic Bone Marrow Mesenchymal Stem Cells: A Randomized Controlled Trial," Transplantation 2015, 99:1681-1690.
Noriega et al., "Intervertebral Disc Repair by Allogeneic Mesenchymal Bone Marrow Cells: A Randomized Controlled Trial," Transplantation 2017, 101:1945-1951.
Gordon et al., Altered adhesive interactions with marrow stroma of haematopoietic progenitor cells in chronic myeloid leukaemia. Nature. 1987. 328; 342-344.
Gordon et al., Characterisation of Stroma-Dependent Blast Colony-Forming Cells in Human Marrow. Journal of Cellular Physiology. 1987: 130;150-156.
Gordon et al., Colony formation by primitive haemopoietic progenitors in cocultures of bone marrow cells and stromal cells. British Journal of Haematology, 1985, 60, 129-136.
García-sancho et al. Influence of HLA Matching on the Efficacy of Allogeneic Mesenchymal Stromal Cell Therapies of Osteoarthritis and Degenerative Disc Disease, Transplantation Direct, 2017: 3 (9): e205.
Pei et al. Chemical-defined and albumin-free generation of human atrial and ventricular myocytes from human pluripotent stem cells, Stem Cell Research, 2017:19;94-103.

* cited by examiner

METHOD FOR OBTAINING AN ENRICHED POPULATION OF FUNCTIONAL MESENCHYMAL STEM CELLS, CELLS OBTAINED THEREOF AND COMPOSITIONS AND COMPRISING THE SAME

CROSS-REFERENCE TO RELATED APPLICATIONS

This application is filed under the provisions of 35 U.S.C. § 371 and claims the priority of International Patent Application No. PCT/EP2019/074991, filed on 18 Sep. 2019 entitled "METHOD FOR OBTAINING AN ENRICHED POPULATION OF FUNCTIONAL MESENCHYMAL STEM CELLS, CELLS OBTAINED THEREOF AND COMPOSITIONS COMPRISING THE SAME" in the name of Ana SÁNCHEZ GARCÍA, et al., which claims priority to European Patent Application No. 18382679.1 filed on 20 Sep. 2018, both of which are hereby incorporated by reference herein in their entirety.

FIELD OF THE INVENTION

The present invention provides a method to obtain a composition comprising an enriched population of cryopreserved, restored and transport conditioned functional mesenchymal stem cells, obtained from an ex vivo sample of bone marrow mesenchymal stem cells for hypothermic transport and local administration of said composition comprising an enriched population of cryopreserved, restored and transport conditioned functional mesenchymal stem cells, in therapy. Finally present invention relates to the use of said compositions comprising an enriched population of cryopreserved, restored and transport conditioned functional mesenchymal stem cells, obtained by the described method, in autologous or allogeneic treatment of diseases susceptible to mesenchymal stem cell therapy, either by local or systemic treatments, and more particularly in the treatment of osteoarticular diseases such as degenerative disc disease, osteoarthritis, and bone repair; in lupus erythematosus, graft-versus-host disease, and other autoimmune diseases; in peripheral vascular insufficiency and other cardiovascular diseases.

BACKGROUND OF THE INVENTION

The gold standard of advanced osteoarthritis therapy with clinical impact, is prosthetic replacement. This is especially problematic in young patients, since articular prostheses have a limited duration also being an expensive procedure, issue that justifies exploring new potentially more effective therapeutic methods.

There is a population of non-hematopoietic stem cells in the bone marrow called stromal progenitor cells or mesenchymal stem cells (MSCs). These cells are characterized by their multipotentiality, i.e. their ability to differentiate into other cell types. MSCs have a fibroblast fusiform morphology population, which expresses CD73, CD90 and CD105 antigens and shows absence of hematopoietic antigens, markers of monocytes, macrophages and B lymphocytes. In addition, they retain the ability of in vitro differentiation towards osteoblasts, adipocytes and chondrocytes when maintained in adequate conditioned environments.

The intra-articular infusion of mesenchymal stem cells (MSCs), for example in osteoarthritis, is one of these new lines of research, according to its recognized regenerative and anti-inflammatory potential.

Studies with MSCs in animal models have proven the ability of said MSCs to survive after infusion in the joint human body environment (such as intervertebral discs, knees, etc.) and, to repair cartilage in a dose-dependent manner.

MSCs have, therefore, the ability to regenerate damaged or wrecked tissues such as bone, cartilage, and other tissues. In addition, their ability to modulate immune reactions and to control inflammation has been demonstrated by their action on T lymphocytes.

MSCs can be obtained from different organs and tissues, but bone marrow represents one of its best and most accessible sources.

However, the frequency of MSCs in bone marrow is low and represents only between 0.001 to 0.01% of the bone marrow mononuclear cells. The fact that, for a single systemic treatment, between $1.0 \times 10^6$ to $2.0 \times 10^6$ MSCs per Kg of body weight is generally used, and that in local treatments a single dose administered locally can be as high as $20\text{-}40 \times 10^6$ cells, makes, therefore, the direct collection in situ of such a large quantity from bone marrow not possible.

Cryopreservation allows that several aliquots of bone marrow mesenchymal stem cells may be administered as only one dose, thus avoiding successive interventions on the patient and reducing part of the manufacturing costs. In addition it allows us to eventually perform different doses for the treatment, thus improving the efficacy of the same.

Moreover, cryopreservation is essential to perform allogeneic administration of MSCs, reducing costs and providing a more efficient manner to treat patients when compared with the use of autologous MSCs, which need to be prepared fresh from the same patient to be treated, making the treatment less efficient, more expensive and logistically more complicated.

However, cryopreservation is not a straightforward procedure, and often results in severe cellular lesions, as well as hidden damage which does not manifests when the cells are thawed but only at a later stage. This compromises the functionality of the MSCs, both in their differentiating capabilities, their ability to regenerate damaged tissue and the speed at which said regeneration is performed. In addition, if the cryopreserving agents, such as dimethyl sulfoxide (DMSO), remain in suspension when the MSCs are administered, adverse reactions have been reported, such as nausea, tachycardia, bradycardia, hypotension, etc. On the other hand DMSO added to the cell cultures at concentrations as low as 0.5% decreases the rate of proliferation of MSC in vitro.

On the other hand, the allogeneic pathway opens the possibility of treatment of patients with autoimmune diseases, whose own cells could carry the disease to be treated and therefore be devoid of healing effects. In addition MSC are much less immunogenic than other cell types and do not usually trigger rejection reactions and even the production of anti-HLA antigens against the donor is generally poor or non-detectable (J Garcia-Sancho et al., Transplantation direct 3 (9): e205).

At present, there are several works featuring cryopreserved mesenchymal cells injection in the bloodstream after thawing, directly and without previous treatments. However, the local inoculation of MSCs into the articular cavity in osteoarthritis treatments, or into the intervertebral disc in degenerative disc disease, is always preferred since all cells are able to arrive to the site to be treated and are scarcely susceptible to be attacked by the host immune system when the treatment is allogeneic. On the other hand, local treatment requires the previous removal of the cryoprotectant agent, otherwise, the cryoprotectant agent, often dimethyl sulphoxyde (DMSO), interferes with multiplication of MSCs. Even when the DMSO is removed, cells with hidden damage are not detected with viability or metabolic assays and, as explained, said hidden damage compromises their viability once administered, as well the functionality, both in their differentiating capabilities, their ability to regenerate damaged tissue and the speed at which said regeneration is performed.

For instance, Marquez-Curtis et al. (Cryobiology 71 (2015) 181-197) provide a review on how the different conditions/processes used to cryopreserve and to thaw mesenchymal stem cells result in a diverse cell viability and growth capability of the cell products obtained. In particular, said review, proposes multiple solutions to improve the properties of the cell products obtained after cryopreservation. On one hand Marquez-Curtis et al, describe different protocols modulating the conditions for cryopreservation (freeze rate, storage temperature, % of cryoprotectant) with use of dimethyl sulfoxide (DMSO) to improve cell product quality after thaw and to limit toxicity of DMSO. On the other hand, the authors also propose other cryoprotectants, such as: glycerol; sugars, such as trehalose, raffinose, lactose, sucrose, etc.; antioxidants; apoptotic inhibitors or mixtures thereof; along with processes such as: vitrification; freezing in a magnetic field; etc., to try to keep the quality of the cell products obtained after thawing, while avoiding toxicity issues, specially derived from the use of DMSO.

While reviewing the status of cryopreservation, said article indicates that it is known that after thawing a significant loss in the recovery of viable cells occurs, the authors merely suggest a variety of possible solutions which include, culturing cells post-thaw, without indication of culturing conditions, culturing cells before cryopreservation, using chemical modulators, as resveratrol or salubrinal, to decrease apoptosis, without providing any particular lead among those suggestions.

Wei et al. (Veterinary surgery, 2018; 47:19-29) also recognize the toxicity issues of DMSO and admit the practical complications for its removal, indicating that, the use of said cryoprotectant results in cell loss and lower number of colony forming units. In this sense, this article points out towards the development of other cryoprotectants, different from DMSO, as a lead to develop stem cell products with adequate phenotype, differentiation and viability profiles, which can be used directly after thawing avoiding the toxicity issues of DMSO.

In the same line, Yuan et al. (Cryotherapy, 2016: 18: 860-869) agree on the need to replace DMSO because of its toxicity issues, and propose ZENALB® 4.5 (a protein supplement) as cryoprotectant to replace DMSO and to obtain cell products which, directly after thawing, have adequate phenotype, differentiation and viability profiles.

The international patent application publication WO 2010/064054 A1 follows, as well, the same line of development, describing the toxicity of the commonly used cryoprotectant DMSO. The publication proposes, instead, compositions with Hypothermosol® and the antioxidant 6-hydroxy-2,5,7,8-tetramethylchroman-2-carboxylic acid (trolox) to store stem cells, including mesenchymal stem cells, but also to cryopreserve them, without the need of DMSO as cryoprotectant. Once more, document WO 2010/064054 A1 proposes the direct use of the cells after thaw.

International patent application publication WO 2017/068140 A1 describes stem cell therapies based on adipose-derived cells. Said publication proposes a method in which stem cells obtained from the stromal vascular fraction of a lipoaspirate are cultured in a bioreactor and consequently frozen and thawed, at least twice, and administered directly after thawing.

It is, therefore, found that the prior art suggests, as a general lead to develop cell products, including mesenchymal stem cell products, which can be used in treatment after cryopreservation, the replacement of DMSO to avoid the viability and toxicity issues encountered, as well as the direct use of the cell product after thaw.

On the other hand, Alves et al. (Tissue Engineering; part A, vol. 19, numbers 7 and 8, 2013) analyze the effect of oxidative stress suffered by MScs during ex vivo culturing and the gradual loss of differentiation potential and reduced clinical efficacy. To this end, the authors propose the use of trolox as antioxidant to prevent said oxidative damage. However, the authors conclude that while trolox supplementation can reduce the oxidative damage during early culture periods, the beneficial effects shown by antioxidants were, nevertheless, unable to rescue human MSCs differentiation capacity after in vitro expansion.

To this end, it is clear that the main key issue to develop efficient and standardized MSC based therapies is to make sure that the manipulation of said cells, such as cryopreservation or expansion, will not damage the cells compromising their activity, such as the capacity to multiply and differentiate once administered.

Further, it is essential to formulate the MSCs in a composition which is able to retain, during transport and until its administration, their functionality and viability, which are generally lost within some hours.

The invention provides a method to obtain an enriched population of cryopreserved, restored and transport conditioned functional MSCs which are formulated in compositions developed for hypothermic transport and local administration, which solves the above-mentioned issues.

BRIEF DESCRIPTION OF THE INVENTION

Present invention relates to a method for obtaining a composition comprising an enriched population of cryopreserved, restored and transport conditioned functional mesenchymal stem cells suitable for administration in therapy, said method comprising the steps of:

a. suspending an ex vivo sample of bone marrow mesenchymal stem cells in a cryoprotecting medium comprising 5% to 10% dimethyl sulfoxide at a concentration of $5 \times 10^6$ to $10 \times 10^6$ cells/ml;

b. cryopreserving the sample of bone marrow mesenchymal stem cells, cooling them first to $-70°$ C. to $-90°$ C. for at least 24 hours prior to storing the sample in liquid nitrogen;

c. restoring the sample of bone marrow mesenchymal stem cells, by performing the following steps:

c1. thawing the sample of the bone marrow mesenchymal stem cells by progressively increasing the temperature up to $35$-$39°$ C. during 1 to 5 minutes;

c2. diluting the sample 10 to 30 times the initial sample volume with suitable culture medium;

c3. centrifuging the sample, discarding the supernatant and resuspending the pellet of mesenchymal stem cells in suitable culture medium;

c4. selecting the mesenchymal stem cells with a viability of at least 70%;

c5. seeding the mesenchymal stem cells selected in step (c4) on a plastic support and incubating said mesenchymal stem cells with a suitable culture medium comprising $CO_2$ from 7.5% to 10% and at least 5% fetal bovine serum, at a cell concentration between 1000 to 5000 cells/cm², with adequate culture conditions at 35-39° C., c6. replacing with fresh suitable culture medium comprising $CO_2$ from 7.5% to 10% and at least 5% fetal bovine serum, at regular time intervals and isolating the cryopreserved and restored functional mesenchymal stem cells from the support when the cells occupy 80 to 100% of the support's surface;

d. suspending the enriched population of cryopreserved and restored, functional mesenchymal stem cells isolated in step (c6) in an adequate medium for transport and storage at 2-8° C. to obtain a composition comprising an enriched population of cryopreserved, restored and transport conditioned, functional mesenchymal stem cells, wherein said adequate medium for transport and storage at 2-8° C. is an isotonic medium comprising 6-hydroxy-2,5,7,8-tetramethylchroman-2-carboxylic acid 0.25 to 1 mM.

Present invention further relates to a composition comprising an enriched population of cryopreserved, restored and transport conditioned functional mesenchymal stem cells obtainable by the method of the invention.

Further, present invention also relates to a composition comprising an enriched population of cryopreserved, restored and transport conditioned functional mesenchymal stem cells obtainable by the method of the invention, for use as a medicament.

DESCRIPTION OF THE INVENTION

Present invention relates to a method for obtaining a composition comprising an enriched population of cryopreserved, restored and transport conditioned functional mesenchymal stem cells (MSCs) in vitro. Said method comprises the steps of:

a. suspending an ex vivo sample of bone marrow mesenchymal stem cells in a cryoprotecting medium comprising 5% to 10% dimethyl sulfoxide at a cell concentration of $5 \times 10^6$ to $10 \times 10^6$ cells/ml;

b. cryopreserving the sample of bone marrow mesenchymal stem cells by decreasing temperature, cooling them first to −70° C. to −90° C. for at least 24 hours prior to storing the sample in liquid nitrogen;

c. restoring the sample of bone marrow mesenchymal stem cells, performing the following steps:
c1. thawing the sample of the bone marrow mesenchymal stem cells by progressively increasing the temperature up to 35-39° C. during 1 to 5 minutes;
c2. diluting the sample 10 to 30 times the sample volume with suitable culture medium;
c3. centrifuging the sample, discarding the supernatant and resuspending the mesenchymal stem cells in suitable culture medium;
c4. selecting the mesenchymal stem cells with a viability of at least 70%;
c5. seeding the mesenchymal stem cells selected in step (c4) on a plastic support and incubating said mesenchymal stem cells with a suitable culture medium comprising 7.5% to 10% $CO_2$ and at least 5% fetal bovine serum, at a concentration between 1000 to 5000 cells/cm², with adequate culture conditions at 35-39° C.,
c6. replacing with fresh suitable culture medium comprising 7.5% to 10% $CO_2$ and at least 5% fetal bovine serum, at regular time intervals and isolating the enriched population of cryopreserved, restored functional mesenchymal stem cells from the support when the cells occupy 80 to 100% of the support's surface;

d. suspending the enriched population of cryopreserved and restored functional mesenchymal stem cells isolated in step (c6) in an adequate medium for transport and storage at 2-8° C. to obtain a composition comprising an enriched population of cryopreserved, restored and transport conditioned functional mesenchymal stem cells, wherein said adequate medium for transport and storage at 2-8° C. is an isotonic medium comprising 6-hydroxy-2,5,7,8-tetramethylchroman-2-carboxylic acid 0.25 to 1 mM.

The suitable culture medium comprises at least 5% fetal bovine serum with 7.5% to 10% $CO_2$ and the required amount of $^-HCO_3$. In this sense, the proportion of $CO_2$ and $^-HCO_3$ in the suitable culture medium remains constant, including a concentration of $CO_2$ from 7.5% to 10%, and at least 5% fetal bovine serum.

Preferably said method further comprising an additional step (c7) of selecting an enriched population of cryopreserved, restored and transport conditioned functional mesenchymal stem cells that:
show adherence to plastic; and
present a viability of at least 70%; and
present an expression ≥90% of CD90, CD166, CD73 and CD105; and
present an expression ≤10% of CD14, CD34, CD45 and HLA-DR ≤10%; and
do not feature chromosomal aberrations; and
present capacity to differentiate into osteoblasts, adipocytes and chondrocytes.

The term "isotonic medium", for the purposes of present invention, refers to a solution that preserves the volume of the cells by having the same effective osmolarity, or non-permeable solute concentration than the cells, i.e. has the same osmotic pressure than the interior of the cells. Accordingly, isotonic solutions allow free exchange of water across the membrane when cells are suspended in said solutions and maintain the volume of the cells suspended therein.

The 6-hydroxy-2,5,7,8-tetramethylchroman-2-carboxylic acid, or trolox is a vitamin E analog. In a more preferred embodiment said adequate medium for transport and storage at 2-8° C. is an isotonic medium comprising 6-hydroxy-2,5,7,8-tetramethylchroman-2-carboxylic acid 0.25 mM to 1 mM is an animal component-free serum-free protein-free medium comprising 6-hydroxy-2,5,7,8-tetramethylchroman-2-carboxylic acid 0.25 mM to 1 mM.

In a more preferred embodiment said isotonic medium comprising 6-hydroxy-2,5,7,8-tetramethylchroman-2-carboxylic acid 0.25 mM to 1 mM is a medium comprising $Na^+$ 100 mM, $K^+$ 42.5 mM, $Ca^{2+}$ 0.05 mM, $Mg^{2+}$ 5 mM, Chloride 17 mM, dihydrogen phosphate 10 mM, $HCO_3$ 5 mM, 4-(2-hydroxyethyl)-1-piperazineethanesulfonic acid (HEPES) 25 mM, lactobionate 100 mM, sucrose 20 mM, mannitol 20 mM, dextran with an average molecular weight of 40000 6%, adenosine 2 mM, glutathione 3 mM, glucose 5 mM, human serum albumin 0.5% and 6-hydroxy-2,5,7,8-tetramethylchroman-2-carboxylic acid 1 mM.

In another preferred embodiment said isotonic medium comprises a 1:9 to 9:1 mixture (v/v) of a first composition comprising $Na^+$ 130 mM, $K^+$ 4 mM, $Ca^{2+}$ 1.35 mM, Chloride 109 mM and lactate 16 mM, with a second composition comprising $Na^+$ 159 mM, $K^+$ 5 mM, $Mg^{2+}$ 0.8 mM, Chloride 77 mM, dihydrogen phosphate 28 mM, citrate 10 mM and acetate 32 mM, supplemented with glucose 5 mM, human serum albumin 0.1% to 0.5% and 6-hydroxy-2,5,7,8-tetramethylchroman-2-carboxylic acid 0.25 to 1 mM.

In a more preferred embodiment said isotonic medium comprises a 1:9, or a 1:4, or a 1:3 or a 1:1, or a 3:1 or a 4:1 or a 9:1 mixture (v/v) of said first composition and said second composition, supplemented with glucose 5 mM, human serum albumin 0.1% to 0.5% and 6-hydroxy-2,5,7,8-tetramethylchroman-2-carboxylic acid 0.25 to 1 mM.

In a more preferred embodiment said isotonic medium comprises a 1:1 mixture (v/v) of said first composition and said second composition, supplemented with glucose 5 mM, human serum albumin 0.5% and 6-hydroxy-2,5,7,8-tetramethylchroman-2-carboxylic acid 0.5 mM In a yet more preferred embodiment said isotonic medium comprises glucose 5 mM, human serum albumin 0.5% and 6-hydroxy-2,5,7,8-tetramethylchroman-2-carboxylic acid 0.5 mM.

In a yet more preferred embodiment said isotonic medium comprises human serum albumin 0.5% and 6-hydroxy-2,5,7,8-tetramethylchroman-2-carboxylic acid 1 mM.

Present invention also refers to a composition comprising an enriched population of cryopreserved, restored and transport conditioned functional mesenchymal stem cells suitable for administration in therapy obtainable according to the method for obtaining a functional population of mesenchymal stem cells (MSCs) in vitro, described above herein.

An embodiment of present invention refers to a composition comprising an enriched population of cryopreserved, restored and transport conditioned functional mesenchymal stem cells, obtainable according to the method described above herein, for use as a medicament, in particular for use in the treatment of diseases susceptible to mesenchymal stem cell therapy.

Another embodiment refers to a composition comprising an enriched population of cryopreserved, restored and transport conditioned functional mesenchymal stem cells, obtainable according to the method described above herein, for use in the treatment of diseases susceptible to mesenchymal stem cell therapy, wherein said composition comprising a population of cryopreserved, restored and transport conditioned functional mesenchymal stem cells is administered locally or in systemic treatments.

Another embodiment refers to a composition comprising an enriched population of cryopreserved, restored and transport conditioned functional mesenchymal stem cells, obtainable according to the method described above herein, for use in the treatment of osteoarticular diseases, bone repair; autoimmune diseases and cardiovascular diseases.

In one embodiment the osteoarticular diseases are selected from degenerative disc disease, osteoarthritis, meniscus injuries, and rheumatoid arthritis, In one embodiment the autoimmune diseases are selected from lupus erythematosus, graft-versus-host disease, and systemic sclerosis.

In one embodiment the cardiovascular diseases are selected from peripheral vascular insufficiency, myocardial infarction, stroke, and ischemia.

Said composition comprising said enriched population of cryopreserved, restored and transport conditioned functional MSCs is capable to retain the functionality of the fresh MSCs after thawing and also during hypothermic transport at 2 to 8° C. for at least 72 hours.

For the purposes of present invention, bone marrow mesenchymal stem cells are non-hematopoietic stem cells present in the bone marrow characterized by their mesodermal multipotentiality and which are, accordingly, able to differentiate towards osteoblasts, adipocytes and chondrocytes.

According to present invention, the term "population of functional mesenchymal stem cells" refers to a sample of mesenchymal stem cells which comprises a quantity of mesenchymal stem cells suitable for use in the treatment of diseases susceptible to mesenchymal stem cell therapy, and wherein said sample comprises only mesenchymal stem cells with the functional characteristics of fresh mesenchymal stem cells, i.e. show adherence to plastic; present a viability of at least 70%; present an expression ≥90% of CD90, CD 166, CD73 and CD105; present an expression ≤10% of CD14, CD34, CD45 and HLA-DR ≤10%; do not feature chromosomal aberrations and present capacity to differentiate into osteoblasts, adipocytes and chondrocytes.

For the purposes of present invention "an enriched population of functional mesenchymal stem cells" refers to a group of at least $0.5\times10^6$ functional mesenchymal stem cells which show adherence to plastic; present a viability of at least 70%; present an expression ≥90% of CD90, CD 166, CD73 and CD105; present an expression ≤10% of CD14, CD34, CD45 and HLA-DR ≤10%; do not feature chromosomal aberrations and present capacity to differentiate into osteoblasts, adipocytes and chondrocytes.

For the purposes of present invention, the term "cryopreserved cells" are cells maintained at temperatures of −70° C. or lower which, due to the preservation low temperature, have substantially any metabolic or chemical activity which might cause damage to the cells substantially stopped.

For the purposes of present invention the term "cryopreserved and restored cells" or "cryopreserved and restored sample of mesenchymal stem cells" and equivalent terms, refer to mesenchymal stem cells which have been previously cryopreserved, thawed, diluted, isolated and cultivated in suitable culture medium comprising at least 5% fetal bovine serum, high levels of $CO_2$ at 35-39° C., according to the method of the invention, wherein said cryopreserved and restored cells feature substantially all metabolic and chemical activity of fresh mesenchymal stem cells and have a viability of at least 70%, more preferably a viability of at least 80% and even more preferably a viability of at least 90%.

For the purposes of present invention the term "cryopreserved, restored and transport-conditioned cells" or "cryopreserved, restored and transport conditioned mesenchymal stem cells" and equivalent terms, refers to mesenchymal stem cells which have been previously cryopreserved and restored in suitable culture medium comprising at least 5% fetal bovine serum, high levels of $CO_2$ at 35-39° C. and which, after isolation, are conditioned for transport, in a suspension comprising adequate isotonic medium for transport and storage at 2-8° C. comprising trolox 0.25 mM to 1 mM. In this sense, for the purposes of present invention, the term "conditioned" is equivalent to "conditioned for transport" or "transport-conditioned" or "conditioned for transport and storage at 2-8° C.".

The term "comprise(s)" is interpreted as meaning that it includes a group of features, but that it does not exclude the presence of other features, as long as they do not render the claim unworkable. To this end, for the purposes of present invention, the term "comprises" may be replaced by the term "consisting of" and the term "consisting essentially of". In this manner, when the term "comprise(s)" is referred to a group of features A, B and C, it should be interpreted as eventually including other features different from A, B and C, as long as they do not render the claim unworkable, but also may be interpreted to only include said features A, B, and C, or to include only substantially said features and, accordingly, "comprise(s)" should be interpreted to also include a group "consisting of" features A, C and C and a group "consisting essentially of" features A, B and C.

The mesenchymal stem cells used in the method of the invention are originated from ex vivo bone marrow mononuclear cells. Said ex vivo bone marrow mononuclear cells include several types of ex vivo marrow stem cells, including ex vivo hematopoietic stem cells, ex vivo mesenchymal stem cells, ex vivo endothelial progenitor cells and other precursor stem cells.

After trauma, cell growth factors may be able to promote tissue differentiation of the bone marrow MSCs therefore making possible the repair of the injured organs and restoration of organ function.

MSCs feature strong adhesion to the plastic in culture. This adhesion ability is used for the isolation and purification of said MSCs from bone marrow mononuclear cells.

Preferably the method for obtaining a composition comprising an enriched population of cryopreserved, restored and transport conditioned functional mesenchymal stem cells suitable for administration in therapy, is carried out in 10 to 15 days.

In a preferred embodiment the ex vivo sample of bone marrow mesenchymal stem cells comprises at least $8 \times 10^6$ bone marrow mesenchymal stem cells.

In a preferred embodiment the ex vivo sample of bone marrow mesenchymal stem cells comprises $8 \times 10^6$ to $10 \times 10^6$ bone marrow mesenchymal stem cells.

Preferably, the ex vivo sample comprises bone marrow mesenchymal stem cells with a viability of at least 90%.

Preferably, the ex vivo sample comprises $8 \times 10^6$ to $10 \times 10^6$ mesenchymal stem cells with a viability of at least 90%, with expression of CD90, CD 166, CD73 and CD105 $\geq$90% and with expression of CD14, CD34, CD45 and HLA-DR $\leq$10%.

In a preferred embodiment, the ex vivo bone marrow mesenchymal stem cell sample is provided in a plastic support, separated from the plastic support using an enzymatic method and, resuspended a suitable medium.

Preferred plastic supports are hydrophilic plastic supports or negatively charged plastic supports. In a preferred embodiment said preferred plastic support comprise hydrophilic groups. In another embodiment said preferred plastic supports are tissue-treated plastic supports having a hydrophilic character. Commercial examples of said preferred plastic supports are Corning CellBIND® supports.

In a preferred embodiment, prior to step (a) the following steps are conducted:
 i. washing with suitable medium the ex vivo bone marrow mesenchymal stem cell sample in a plastic support;
 ii. adding an enzymatic solution and incubate at suitable conditions for the medium used;
 iii. inactivating the enzymatic solution by adding equal volume of medium;
 iv. centrifuging and discard the supernatant.

In a preferred embodiment the suitable medium for washing the cells in step (i) is Dulbecco's Modified Eagle Medium (DMEM).

In another preferred embodiment step (i) is carried out in a culture medium selected from Iscove's Modified Dulbecco's Medium (IMDM), Reduced Serum Media of Eagle's Minimum Essential Media, Eagle's Minimum Essential Medium, modified Eagle's Minimum Essential Medium with nucleosides, glucose, etc., or any other suitable culture medium.

In a preferred embodiment, when the suitable medium is DMEM, step (ii) comprises adding an enzymatic solution and incubating during 5 to 10 minutes at 35-37° C. under 10% $CO_2$, more preferably at 37° C.

In any case, the skilled person will recognize which are the possible culture medium and conditions, as well as the modifications possible to conduct the culture of step (i).

Preferably, the enzymatic solution used in step (ii) comprises 0.05% trypsin and 0.02% tetra sodium ethylenediaminetetraacetic acid (EDTA) in Hanks' Balanced Salt Solution.

A commercial example of the enzymatic solution used in step (ii) is a Trypsin-EDTA 1× solution (Sigma 9417C) Preferably, step (iv) comprises centrifuging the sample at 300 to 500 g at 15 to 25° C. for 5 to 10 minutes, more preferably at 400 g at 20° C. for 5 minutes.

In a preferred embodiment, step (a) comprises providing a sample of $8 \times 10^6$ to $10 \times 10^6$ mesenchymal stem cells with a viability of at least 90%, with expression of CD90, CD 166, CD73 and CD105 $\geq$90% and with expression of CD14, CD34, CD45 and HLA-DR $\leq$10%.

Preferably, the ex vivo sample of bone marrow mesenchymal stem cells used in step (a) are obtained by a method comprising the steps of:
 I. providing an ex vivo sample of at least 30 ml of filtered bone marrow aspirate;
 II. subjecting the ex vivo bone marrow aspirate to an anticoagulant;
 III. selecting the mononuclear cells from the ex vivo bone marrow aspirate;
 IV. select the mononuclear cells with a viability higher than 70%;
 V. seeding the mononuclear cells at $1.5 \times 10^6$ to $2 \times 10^6$ cells/cm$^2$ in a plastic support, in a suitable culture medium and incubating them in adequate culture conditions;
 VI. measuring the cell growth percentage and the appearance of mesenchymal stem cells adhered to the plastic support at regular time intervals and
  VI.1 changing the culture medium when the cell growth percentage is lower than 60%, removing the supernatant; or
  VI.2 isolating the sample of mesenchymal stem cells adhered to the plastic support if the cell growth percentage is higher than 80%;
  VI.3 performing subcultures up to 2 passages in order to increase and purify said mesenchymal stem cells and isolating the mesenchymal stem cells adhered to the plastic support from each of the subcultures if the growth percentage is higher than 80%.

Preferably the method to obtain an ex vivo sample of bone marrow mesenchymal stem cells of step (a), from an ex vivo sample of bone marrow aspirate, is carried out in 8 to 10 days.

In one embodiment, the anticoagulant used in step (II) is heparin.

In one embodiment step (III) comprises selecting the mononuclear cells from the ex vivo bone aspirate by density gradient.

Preferably step (Ill) comprises selecting in vitro the mononuclear cells from the ex vivo bone aspirate by density gradient using a solution comprising ficoll, comprising:
 III.1 adding slowly a ficoll solution to the ex vivo bone marrow aspirate sample;
 III.2 centrifuging at the sample at 300 to 500 g, at 15 to 25° C. for at least 30 minutes without brake;

III.3 isolating and washing the interface with a suitable medium;
III.4 centrifuging and discarding the supernatant;
III.5 washing the pellet with a suitable medium;
III.6 centrifuging and discarding the supernatant;
III.7 resuspending the pellet with the mononuclear cells in a suitable culture medium; In a preferred embodiment step I comprises adding slowly a Ficoll solution in a proportion 2:3 (vol:vol) to the ex vivo bone marrow aspirate sample.

In a preferred embodiment washing is carried out with phosphate buffer containing 0.5 Human Serum albumin.

In another preferred embodiment washing is carried out with a physiological saline solution in step III.3.

In another preferred embodiment washing is carried out with Ringer's solution.

Preferably, step III.4 comprises centrifuging the sample at 300 to 500 g at 15 to 25° C. for 5 to 10 minutes, more preferably at 400 g at 20° C. for 5 minutes.

Preferably, step III.6 comprises centrifuging the sample at 300 to 500 g at 15 to 25° C. for 5 to 10 minutes, more preferably at 400 g at 20° C. for 5 minutes.

In a preferred embodiment the mononuclear cells selected in step (IV) have a viability higher than 70%, more preferably higher than 80% and most preferably higher than 90%.

Preferably, the mononuclear cell viability is determined using a dye-exclusion test. Said dye-exclusion tests are based on the principle that live cells possess intact cell membranes that exclude certain dyes, such as trypan blue, whereas dead cells do not. In this test, a cell suspension is simply mixed with dye and then visually examined to determine whether cells take up or exclude dye. Cells excluding the dye are therefore live cells.

In a preferred embodiment step V is carried out in a culture medium selected from Iscove's Modified Dulbecco's Medium (IMDM), Reduced Serum Media of Eagle's Minimum Essential Media, Eagle's Minimum Essential Medium, modified Eagle's Minimum Essential Medium with nucleosides, glucose, etc., or any other adequate culture medium.

In a preferred embodiment step V is carried out seeding the mononuclear cells at $1.5 \times 10^6$ to $2 \times 10^6$ cells/cm$^2$ in a plastic support, in DMEM with at least 5% fetal bovine serum (FBS) and incubating at 35-39° C. under 7.5% to 10% $CO_2$. The culture medium comprises preferably, at least 5% fetal bovine serum with 7.5% to 10% $CO_2$ and the required amount of $^-HCO_3$.

In another preferred embodiment step V is carried out seeding the mononuclear cells at $1.5 \times 10^6$ to $2 \times 10^6$ cells/cm$^2$ in a plastic support, in DMEM, with at least 5% FBS and 0.5% gentamycin and incubating at 35-39° C. under 7.5-10% $CO_2$.

Preferred plastic supports are hydrophilic plastic supports or negatively charged plastic supports. In a preferred embodiment said preferred plastic support comprise hydrophilic groups. In a preferred embodiment said preferred plastic supports are tissue-treated plastic supports having a hydrophilic character. Commercial examples of said preferred plastic supports are Corning CellBIND® supports.

In any case, the skilled person will recognize which are the possible culture medium and conditions, as well as the modifications possible to conduct the culture of step (V).

Preferably, in step VI, if the cell growth percentage is less than 60-80% a change of medium is made.

Preferably, in step VI if it was greater than 80% the cell culture is submitted to cell dissociation and expansion by performing subcultures up to 2 passages in order to increase and purify the cell line of MSCs.

In a preferred embodiment step (VI.3) comprises isolating the mesenchymal stem cells adhered to the plastic support from each of the subcultures if the cell growth percentage is higher than 80%; wherein isolating comprises:
i. washing with suitable medium the bone marrow mesenchymal stem cell sample in a plastic support;
ii. adding an enzymatic solution and incubate at adequate conditions for the medium used;
iii. inactivating the enzymatic solution by adding equal volume of medium;
iv. centrifuging and discard the supernatant.

In a preferred embodiment the suitable medium for washing the cells in step (i) is Dulbecco's Modified Eagle Medium (DMEM).

In a preferred embodiment, when the suitable medium is DMEM, step (ii) comprises adding an enzymatic solution and incubating during 5 to 10 minutes at 35 to 39° C. under 10% $CO_2$.

Preferably, the enzymatic solution used in step (ii) is a solution containing 0.05% trypsin and 0.02% and 0.05% sodium ethylenediaminetetraacetic acid. Preferably, the enzymatic solution used in step (ii) comprises 0.05% trypsin and 0.02% tetra sodium ethylenediaminetetraacetic acid (EDTA) in Hanks' Balanced Salt Solution.

Preferably the centrifuging of step (iv) is carried out at 300-500 g at 15 to 25° C. and during 30 minutes.

In any case, the skilled person will recognize which are the possible different media and conditions, as well as the modifications possible to conduct the isolation of the mesenchymal stem cells of step (VII).

In a preferred embodiment the ex vivo sample of mesenchymal stem cells obtained above, for use in step (a), have a viability of at least 90%, with expression of CD90, CD 166, CD73 and CD105 ≥90% and with expression of CD14, CD34, CD45 and HLA-DR ≤10%.

In a preferred embodiment the ex vivo bone marrow aspirate sample contains more than 3000 leukocytes/μl.

In a preferred embodiment the ex vivo bone marrow aspirate sample is an ex vivo iliac crest marrow aspirate sample.

In a preferred embodiment the cryoprotecting medium of step (a) comprises a medium comprising Fetal Bovine Serum and 5 to 10% DMSO.

In another preferred embodiment the cryoprotecting medium of step (a) comprises 5% DMSO and 95% fetal bovine serum.

In another preferred embodiment the cryoprotecting medium of step (a) comprises 10% DMSO and 90% fetal bovine serum.

In another preferred embodiment the cryoprotecting medium of step (a) comprises an animal component-free serum-free protein-free medium comprising 5% DMSO.

In yet another preferred embodiment the cryoprotecting medium of step (a) comprises an animal component-free serum-free protein-free medium comprising 10% DMSO.

In a preferred embodiment the cryoprotecting medium of step (a) comprises 5 to 10% DMSO, and 95 to 90% of an isotonic composition comprising Na+ 100 mM, K+ 42.5 mM, Ca2+ 0.05 mM, Mg2+ 5 mM, Chloride 17 mM, dihydrogen phosphate 10 mM, $HCO_3^-$ 5 mM, 4-(2-hydroxyethyl)-1-piperazineethanesulfonic acid (HEPES) 25 mM, lactobionate 100 mM, sucrose 20 mM, mannitol 20 mM, dextran with an average molecular weight of 40000 6%, adenosine 2 mM, glutathione 3 mM, glucose 5 mM.

In a preferred embodiment the cryoprotecting medium of step (a) comprises 5% DMSO, and 95 to 90% of an isotonic composition comprising Na+ 100 mM, K+ 42.5 mM, Ca2+

0.05 mM, Mg2+ 5 mM, Chloride 17 mM, dihydrogen phosphate 10 mM, $HCO_3^-$ 5 mM, 4-(2-hydroxyethyl)-1-piperazineethanesulfonic acid (HEPES) 25 mM, lactobionate 100 mM, sucrose 20 mM, mannitol 20 mM, dextran with an average molecular weight of 40000 6%, adenosine 2 mM, glutathione 3 mM, glucose 5 mM.

In a preferred embodiment the cryoprotecting medium of step (a) comprises 10% DMSO, and 95 to 90% of an isotonic composition comprising Na+ 100 mM, K+ 42.5 mM, Ca2+ 0.05 mM, Mg2+ 5 mM, Chloride 17 mM, dihydrogen phosphate 10 mM, $HCO_3^-$ 5 mM, 4-(2-hydroxyethyl)-1-piperazineethanesulfonic acid (HEPES) 25 mM, lactobionate 100 mM, sucrose 20 mM, mannitol 20 mM, dextran with an average molecular weight of 40000 6%, adenosine 2 mM, glutathione 3 mM, glucose 5 mM.

In a preferred embodiment step (b) comprises cryopreserving the sample of bone marrow mesenchymal stem cells at a speed of 1° C./min until −70° C. to −90° C. for at least 25 hours prior to storing the sample in liquid nitrogen, Preferably, step (c) of restoring the cryopreserved mesenchymal stem cells starts in accordance to the date established for treatment which can be in up to 6 to 20 years.

Preferably, step (c1) is carried out quickly, in 15 to 20 minutes.

Preferably step (c1) comprises thawing the cryopreserved mesenchymal stem cells by progressively increasing the temperature up to 35-39° C. during 1 to 5 minutes, while maintaining a controlled speed of temperature increase. An adequate equipment to thaw the cryopreserved mesenchymal stem cells in step (c1) is a ThawSTAR® CFT2.

In a preferred embodiment, the suitable culture medium of step (c2) is Dulbecco's Modified Eagle Medium with at least 5% Fetal Bovine Serum and 7.5% to 10% $CO_2$. The culture medium comprises preferably, at least 5% fetal bovine serum with 7.5% to 10% $CO_2$ and the required amount of $^-HCO_3$.

In another preferred embodiment, the suitable culture medium of step (c2) is selected from Iscove's Modified Dulbecco's Medium (IMDM), Reduced Serum Media of Eagle's Minimum Essential Media, Eagle's Minimum Essential Medium, modified Eagle's Minimum Essential Medium with nucleosides, glucose, etc., or any other adequate culture medium including 7.5% to 10% $CO_2$ and at least 5% Fetal Bovine Serum.

In any case, the skilled person will recognize which are the possible culture medium comprising at least 5% FBS and high levels of $CO_2$ and $^-HCO_3$, and conditions at 35-39° C., as well as the modifications possible to conduct the culture of step (c2).

Preferably, step (c3) comprises centrifuging the sample, discarding the supernatant and resuspending the mesenchymal stem cells in suitable culture medium at a concentration of $1\times10^6$ to $5\times10^6$ cells/ml. Preferably, said suitable culture medium includes 7.5% to 10% $CO_2$ and at least 5% Fetal Bovine Serum.

Preferably, step (c3) comprises centrifuging the sample at 300 to 500 g at 15 to 25° C. for 5 to 10 minutes, more preferably at 400 g at 20° C. for 5 minutes.

Preferably, the cell viability of the mesenchymal stem cells, in step (c4), is determined using a dye-exclusion test.

Preferably, the cell viability of the mesenchymal stem cells, in step (c4), is determined using Trypan Blue.

Said dye-exclusion tests are based on the principle that live cells possess intact cell membranes that exclude certain dyes, such as trypan blue, Eosin, or propidium, whereas dead cells do not. In this test, a cell suspension is simply mixed with dye and then visually examined to determine whether cells take up or exclude dye. Cells excluding the dye are therefore live cells.

Preferably, step (c6) comprises replacing with fresh adequate culture medium, comprising high levels of $CO_2$, preferably at least 5% Fetal Bovine Serum and 7.5% to 10% $CO_2$, at regular time intervals and isolating the enriched population of cryopreserved and restored functional mesenchymal stem cells from the support when the cells occupy 80 to 100% of the support's surface.

In a preferred embodiment, the suitable culture medium of step (c5) and (c6) is Dulbecco's Modified Eagle Medium with 7.5% to 10% $CO_2$, with the required amount of $^-HCO_3$ and at least 5% Fetal Bovine Serum.

In another preferred embodiment, the suitable culture medium of step (c5) and (c6) is selected from Iscove's Modified Dulbecco's Medium (IMDM), Reduced Serum Media of Eagle's Minimum Essential Media, Eagle's Minimum Essential Medium, or any other adequate culture medium with 7.5% to 10% $CO_2$ and at least 5% Fetal Bovine Serum.

Preferably the culture of step (c5) and (c6) will be maintained at 35-39° C. with 7.5% to 10% $CO_2$ with a suitable culture medium comprising at least 5% Fetal Bovine Serum. The culture medium comprises additionally the required amount of $^-HCO_3$.

Preferably the culture of step (c5) will be maintained at the culture conditions adequate for the selected culture medium.

In any case, the skilled person will recognize which are the possible culture medium and conditions 35-39° C., as well as the modifications possible to conduct the culture of step (c5) and (c6) comprising high levels of $CO_2$ and at least 5% Fetal Bovine Serum.

Preferably, in step (CS) the medium is changed every 3 to 4 days until the cells occupy 80-100% of the growing surface, obtaining a yield of 10000 to 40000 cells/cm$^2$. Preferably step (CS) is carried out in 10 to 15 days.

In a preferred embodiment step (c6) comprises isolating the enriched population of cryopreserved and restored functional mesenchymal stem cells from the support when the cells occupy 80 to 100% of the support's surface; wherein isolating comprises:
  i. washing with suitable medium the cryopreserved, restored and functional mesenchymal stem cell sample in a plastic support;
  ii. adding an enzymatic solution and incubating at adequate conditions for the medium used;
  iii. inactivating the enzymatic solution by adding equal volume of medium;
  iv. centrifuging and discarding the supernatant.

In a preferred embodiment the suitable medium for washing the cells in step (i) is Dulbecco's Modified Eagle Medium (DMEM).

In a preferred embodiment, when the suitable medium is DMEM, step (ii) comprises adding an enzymatic solution and incubating during 5 to 10 minutes at 35-39° C. under 7.5% to 10% $CO_2$.

Preferably, the enzymatic solution used in step (ii) is a solution containing 0.05% trypsin and 0.02% ethylenediaminetetraacetic acid. Preferably, the enzymatic solution used in step (ii) comprises 0.05% trypsin and 0.02% tetra sodium ethylenediaminetetraacetic acid (EDTA) in Hanks' Balanced Salt Solution.

In any case, the skilled person will recognize which are the possible different media and suitable conditions, as well as the modifications possible to conduct the isolation of the enriched population of cryopreserved and restored functional mesenchymal stem cells of step (c6).

Preferably the centrifuging of step (iv) is carried out at 300-500 g at 15 to 25° C. and during 10 to 30 minutes, more preferably at 400 g, 20° C. during 10 minutes.

In a preferred embodiment, the enriched population of cryopreserved and restored functional mesenchymal stem cells isolated in step (c6) have a viability ≥80%.

In a preferred embodiment, the enriched population of cryopreserved and restored functional mesenchymal stem cells isolated in step (c6) have a viability ≥90%.

In a preferred embodiment said adequate medium for transport and storage at 2-8° C. is an isotonic medium comprising 6-hydroxy-2,5,7,8-tetramethylchroman-2-carboxylic acid (trolox) 0.25 mM to 1 mM.

The 6-hydroxy-2,5,7,8-tetramethylchroman-2-carboxylic acid, or trolox is a vitamin E analog.

In a more preferred embodiment said isotonic medium comprising 6-hydroxy-2,5,7,8-tetramethylchroman-2-carboxylic acid 0.25 mM to 1 mM is an animal component-free serum-free protein-free medium comprising 6-hydroxy-2,5,7,8-tetramethylchroman-2-carboxylic acid 0.25 mM to 1 mM.

In a more preferred embodiment said isotonic medium comprising 6-hydroxy-2,5,7,8-tetramethylchroman-2-carboxylic acid 0.25 mM to 1 mM is a medium comprising $Na^+$ 100 mM, $K^+$ 42.5 mM, $Ca^{2+}$ 0.05 mM, $Mg^{2+}$ 5 mM, Chloride 17 mM, dihydrogen phosphate 10 mM, $HCO_s$-5 mM, 4-(2-hydroxyethyl)-1-piperazineethanesulfonic acid (HEPES) 25 mM, lactobionate 100 mM, sucrose 20 mM, mannitol 20 mM, dextran with an average molecular weight of 40000 6%, adenosine 2 mM, glutathione 3 mM, glucose 5 mM, human serum albumin 0.5% and 6-hydroxy-2,5,7,8-tetramethylchroman-2-carboxylic acid 1 mM.

In another preferred embodiment said isotonic medium comprises a 1:9 to 9:1 mixture (v/v) of a first composition comprising $Na^+$ 130 mM, $K^+$ 4 mM, $Ca^{2+}$ 1.35 mM, Chloride 109 mM and lactate 16 mM, with a second composition comprising $Na^+$ 159 mM, $K^+$ 5 mM, $Mg^{2+}$ 0.8 mM, Chloride 77 mM, dihydrogen phosphate 28 mM, citrate 10 mM and acetate 32 mM, supplemented with glucose 5 mM, human serum albumin 0.1% to 0.5% and 6-hydroxy-2,5,7,8-tetramethylchroman-2-carboxylic acid 0.25 to 1 mM.

In a more preferred embodiment said isotonic medium comprises a 1:9, or a 1:4, or a 1:3 or a 1:1, or a 3:1 or a 4:1 or a 9:1 mixture (v/v) of said first composition and said second composition, supplemented with glucose 5 mM, human serum albumin 0.1% to 0.5% and 6-hydroxy-2,5,7,8-tetramethylchroman-2-carboxylic acid 0.25 to 1 mM.

In a more preferred embodiment said isotonic medium comprises a 1:1 mixture (v/v) of said first composition and said second composition, supplemented with glucose 5 mM, human serum albumin 0.5% and 6-hydroxy-2,5,7,8-tetramethylchroman-2-carboxylic acid 0.5 mM In a yet more preferred embodiment said isotonic medium comprises glucose 5 mM, human serum albumin 0.5% and 6-hydroxy-2,5,7,8-tetramethylchroman-2-carboxylic acid 0.5 mM.

In a yet more preferred embodiment said isotonic medium comprises human serum albumin 0.5% and 6-hydroxy-2,5,7,8-tetramethylchroman-2-carboxylic acid 1 mM.

An adequate commercial isotonic medium is Hyperthermosol®-Base supplemented with 1 mM 6-hydroxy-2,5,7,8-tetramethylchroman-2-carboxylic acid, and 0.1% to 0.5% Human Serum Albumin.

The Hyporthermosol®-Base solution contains $Na^+$ 100 mM, $K^+$ 42.5 mM, $Ca^{2+}$ 0.05 mM, $Mg^{2+}$ 5 mM, $Cl^-$ 17.1 mM, dihydrogen phosphate 10 mM, bicarbonate 5 mM, 4-(2-hydroxyethyl)-1-piperazineethanesulfonic acid (HEPES) 25 mM, lactobionate 100 mM, sucrose 20 mM, mannitol 20 mM, glucose 5 mM, adenosine 2 mM and gluthatione 3 mM.

Preferably said method further comprises, an additional step (c7) of selecting an enriched population of cryopreserved, restored and transport conditioned functional mesenchymal stem cells that:
  show adherence to plastic; and
  present a viability of at least 70%; and
  present an expression ≥90% of CD90, CD 166, CD73 and CD105; and
  present an expression ≤10% of CD14, CD34, CD45 and HLA-DR ≤10%; and
  do not feature chromosomal aberrations; and
  present capacity to differentiate into osteoblasts, adipocytes and chondrocytes.

Preferably the composition comprising an enriched population of cryopreserved, restored and transport conditioned functional mesenchymal stem cells suitable for administration in therapy obtained according to the method of the invention, is transported in an isothermal packaging that ensures a constant temperature between 2 and 8° C. for at least >72 hours, at all times of the year and climatic conditions. An example of packaging used with the method of the invention is the ORCA® packaging system.

The composition comprising an enriched population of cryopreserved, restored and transport conditioned functional mesenchymal stem cells remain stable even after undergoing up to 10 duplications.

An embodiment refers to a composition comprising an enriched population of cryopreserved, restored and transport conditioned functional mesenchymal stem cells obtainable according to the method of the invention.

Another embodiment refers to a composition comprising an enriched population of cryopreserved, restored and transport conditioned functional mesenchymal stem cells, obtainable according to the method of the invention, for use as a medicament. Another embodiment refers to the use of a composition comprising a population of cryopreserved, restored and transport conditioned functional mesenchymal stem cells suitable for administration in therapy, obtained according to the method of the invention, for use in the manufacture of a medicament Additionally, the invention refers to a composition comprising an enriched population of cryopreserved, restored and transport conditioned functional mesenchymal stem cells, obtainable according to the method of the invention, for use in the treatment of diseases susceptible to mesenchymal stem cell therapy.

Another embodiment refers to a composition comprising an enriched population of cryopreserved, restored and transport conditioned functional mesenchymal stem cells, obtainable according to the method of the invention, for use in the treatment of diseases susceptible to mesenchymal stem cell therapy, wherein said composition comprising a population of cryopreserved, restored and transport conditioned functional mesenchymal stem cells is administered locally or in systemic treatments.

Another embodiment refers to a composition comprising an enriched population of cryopreserved, restored and transport conditioned functional mesenchymal stem cells obtainable according to the method of the invention, for use in the treatment of osteoarticular diseases, bone repair; autoimmune diseases and cardiovascular diseases.

In one embodiment the osteoarticular diseases are selected from degenerative disc disease, osteoarthritis, meniscus injuries, and rheumatoid arthritis, In one embodiment the autoimmune diseases are selected from lupus erythematosus, graft-versus-host disease, and systemic sclerosis.

In one embodiment the cardiovascular diseases are selected from peripheral vascular insufficiency, myocardial infarction, stroke, and ischemia. In a preferred embodiment the disease is optic nerve ischemic disorder.

For the purposes of present invention the term "autologous treatment", or"autologous therapy", refers to a treatment wherein the bone marrow mesenchymal stem cells used in step (a) of the method of the invention are bone marrow mesenchymal stem cells from the same person as the person for who the enriched population of functional mesenchymal stem cells for use, or for who the composition comprising an enriched population of functional mesenchymal stem cells for use, according to the invention is intended.

For the purposes of present invention the term "allogeneic or allogenic treatment", or "allogeneic therapy" refers to a treatment wherein the bone marrow mesenchymal stem cells used in step (a) of the method of the invention are bone marrow mesenchymal stem cells from a different person than the person for who the enriched population of functional mesenchymal stem cells for use, or for who the composition comprising an enriched population of functional mesenchymal stem cells for use, according to the invention is intended.

The compositions comprising an enriched population of cryopreserved, restored and transport conditioned functional mesenchymal stem cells, obtainable according to the method of the invention, described above herein, are, therefore, used in the manufacture of a medicament for autologous or allogeneic treatment of the treatment of diseases susceptible to mesenchymal stem cell therapy, either by local or systemic treatments, in particular osteoarticular diseases, osteoarthritis, autoimmune disease and cardiovascular diseases.

An embodiment of the invention refers to a composition comprising an enriched population of cryopreserved, restored and transport conditioned functional mesenchymal stem cells, obtainable according to the method of the invention, for use in as a medicament to be administered at a concentration of $5\times10^6$ to $10\times10^6$ cells/ml.

An embodiment of the invention refers to a composition comprising an enriched population of cryopreserved, restored and transport conditioned functional mesenchymal stem cells, obtainable according to the method of the invention, for use in as a medicament to be administered at a cell density of $1\times10^6$ to $10\times10^6$ cells/ml and a dose of 0.5 to 90 million cells, depending on the indication.

An embodiment of the invention refers to a composition comprising an enriched population of cryopreserved, restored and transport conditioned functional mesenchymal stem cells, obtainable according to the method of the invention, described above herein, for use in the autologous treatment of osteoarticular diseases, bone repair; autoimmune diseases and cardiovascular diseases.

Another embodiment refers to a method of treatment of osteoarticular diseases, bone repair; autoimmune diseases and cardiovascular diseases comprising administering a therapeutic amount of a composition comprising a composition comprising an enriched population of cryopreserved, restored and transport conditioned functional mesenchymal stem cells, to a subject in need thereof, wherein said composition comprising said enriched population, are obtainable according to the method described in the present disclosure.

BRIEF DESCRIPTION OF THE FIGURES

Reference

EXAMPLES

Figure 1:
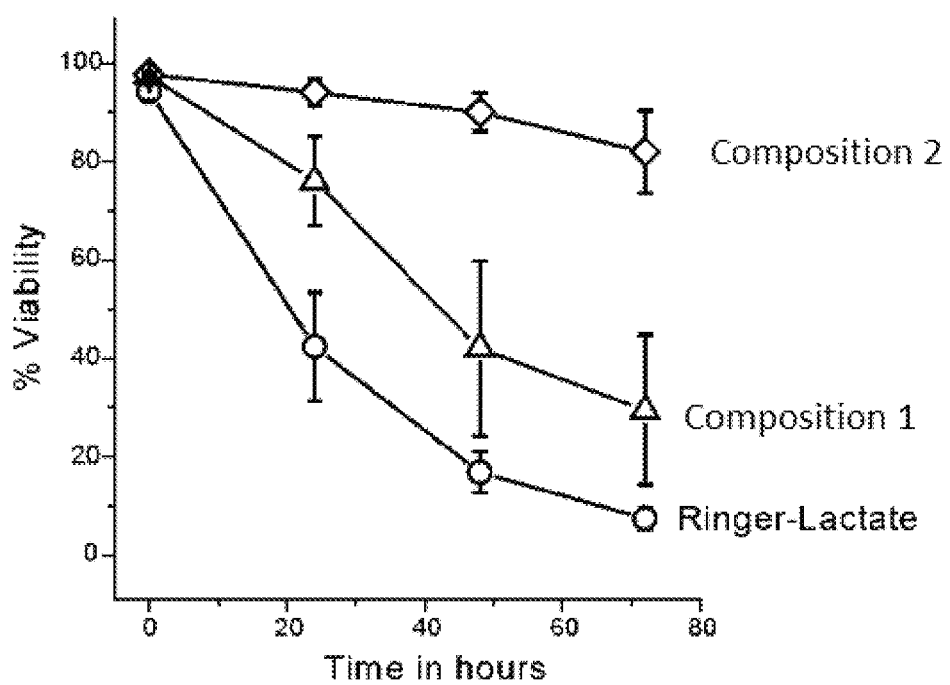
FIG. 1: effects of Composition 2 according to the invention and of reference composition 1 and a composition comprising a Ringer's lactate solution supplemented with glucose and human serum albumin, on cell viability during 3 days storage under hypothermic conditions. (2-8° C.). Data are mean±sem of 5 different donors

The invention is illustrated in the examples, as well as in the figures and generic schemes. The substituents and integers used in the following schemes are as defined in the embodiments of the instant invention, unless otherwise indicated. This section is set forth to aid in an understanding of the invention but should not be construed to limit in any way the invention as set forth in the claims.

The compositions comprising an enriched population of functional mesenchymal stem cells obtained according to the method of the invention and used in the examples have been processed using Good Manufacturing Practice (GMP) at the Cell Production Unit of the Instituto de Biologia y Genética Molecular (IBGM) of Valladolid, following the standard operation procedures approved by the Spanish Medicines Agency, AEMPS (PEI Num.10-134 and PEI num 15-007).

Example 1: Obtaining a Population of Functional Mesenchymal Stem Cells According to the Method of the Invention Bone marrow aspirate subjected to a protocolized anticoagulant procedure is the cellular source for obtaining the MSCs used to obtain the compositions of the example. The bone marrow aspirate was processed within 24 hours after its extraction.

The process of obtaining MSCs approximately lasts 21 to 28 days.

In the first step the mononuclear cell fraction (MNCs) was selected with Ficoll density gradient. Subsequently, a cell viability study was carried out by Trypan Blue exclusion technique: mononuclear cells (MNCs) must have a viability ≥70% to start with culture. MNCs were seeded in culture flasks containing DMEM+20% FBS (if bacterial contamination problems are expected, add 0.5% gentamycin), and were incubated at 37° C. under 10% $CO_2$. Every 3 or 4 days the appearance of the cell monolayer and the confluence (% of the culture surface occupied by the cells) were observed with the inverted microscope. If confluence was less than 60-80% a change of medium was made; if confluence was greater than 80% the cell culture was submitted to cell dissociation and expansion (passage) and subcultures were performed in order to increase number and to purify the cell line of MSC.

The cells obtained during the first passage were washed, quantified and suspended in cryopreservation medium. The cell concentration was set at $5\text{-}10 \times 10^6$ MSC per 1 ml of cryopreservation medium made of 90% FBS+10% DMSO (cryopreservant).

The cryopreservation procedure was performed gradually, maintaining the cells at −80±8° C. for 24-72 hours. After this period of time the cells were stored under liquid nitrogen at nominally −196° C. until use.

The restoration, including re-expansion, of the sample was scheduled in accordance to the date established for treatment which can be in up to 6 to 20 years later.

During the restoration, the cryoprotectants were removed quickly, in 15-20 min, taking into account that the sample must be property tempered to its culture temperature (37° C.).

Finally, the cells were resuspended in complete culture medium to perform counting and cell viability studies, excluding cell batches with less than 70% viability.

Once known the number of viable cells restored, a sample of $5 \times 10^5$ cells was taken for cytogenetic analysis as seen below in this example. The remaining solution was seeded at a concentration between 1000-5000 cells per $cm^2$.

This culture was maintained at 37° C. with 10% $CO_2$. The medium was changed every 4 days until the cells occupied 80-100% of the growing surface. At this moment a dissociation with trypsin-EDTA was carried out. The restoration, including re-expansion time lasts for 10-15 days since the thawing is conducted.

Cell viability was greater than 80% and did not change in about 12 hours.

Example 2: Compositions Comprising an Enriched Population of Functional Mesenchymal Stem Cells, Obtained According to the Method of the Invention The effects of several compositions on cell viability along 3 days storage under hypothermic conditions (2-8° C.) in the functional characteristics of the enriched population of cryopreserved and restored functional mesenchymal stem cells obtained in Example 1, were investigated.

Three different media were used to condition the MSCs for transport, Ringer-Lactate solution, SSP+ platelet additive solution and Hypothermosol-FRS, of which compositions are shown in Table 1.

The following functional actions were investigated combining the three solutions:
1. The K concentration of the medium was increased in order to favor $K^+$ pumping through the membrane Na/K ATPase into the cells and restoration of the alkali-ion gradients, which dissipate because of the inhibition of the plasma membrane Na/K ATPase due to lowering temperature. In addition, the $Mg^{2+}$ content of the medium was increased in order to stabilize the plasma membrane.
2. Buffer capacity (phosphate, citrate, bicarbonate and HEPES) was increased for better maintenance of pH. The presence of lactate and acetate also contributed by decreasing proton production during metabolism.
3. Nutritive potency of the medium was favored by adding metabolic substrates that act through different metabolic pathways such as glucose, acetate and adenosine.
4. Plasma membrane-impermeable osmolytes such as lactobionate, sucrose, mannitol or dextran were added to oppose colloid osmotic cell lysis.
5. Finally, antioxidant capacity was increased by complementation of the medium with glutathione and the soluble vitamin E analog 6-hydroxy-2,5,7,8-tetramethylchroman-2-carboxylic acid (trolox).

The beneficial activity of each one of these additives was investigated to show if the effects of the modification were positive. The different solutions tested are shown in table 1:

TABLE 1

| Composition (mmoles/L) | Ringer's solution with lactate | SSP+ | Composition 1 | Composition 2 | Composition 3 |
|---|---|---|---|---|---|
| Na | 130 | 159 | 145 | 145 | 100 |
| K | 4 | 5 | 4.5 | 4.5 | 42.5 |
| Ca | 1.35 | | 0.7 | 0.7 | 0.05 |
| Mg | | 0.8 | 0.4 | 0.4 | 5 |
| Cl | 109 | 77 | 93 | 93 | 17 |
| $H_2PO_4$ | | 28 | 14 | 14 | 10 |
| $HCO_3$ | 5 | | | | |
| Lactate | 28 | | 14 | 14 | |
| Acetate | | 32 | 16 | 16 | |
| Citrate | | 10 | 5 | 5 | |
| HEPES | | | | | 25 |
| Lactobionate | | | | | 100 |
| Sucrose | | | | | 20 |
| Mannitol | 20 | | | | |
| Dextran-40.% | | | | | 6% |
| Adenosine | | | | | 2 |
| Glutathione | | | | | 3 |
| Trolox | | | | 0.5 | 1 |

TABLE 1-continued

| Composition (mmoles/L) | Ringer's solution with lactate | SSP+ | Composition 1 | Composition 2 | Composition 3 |
|---|---|---|---|---|---|
| Glucose | 5 | | 5 | 5 | 5 |
| HSA, % | 0.1-0.5% | | 0.5% | 0.5% | 0.5% |

Figure 2:
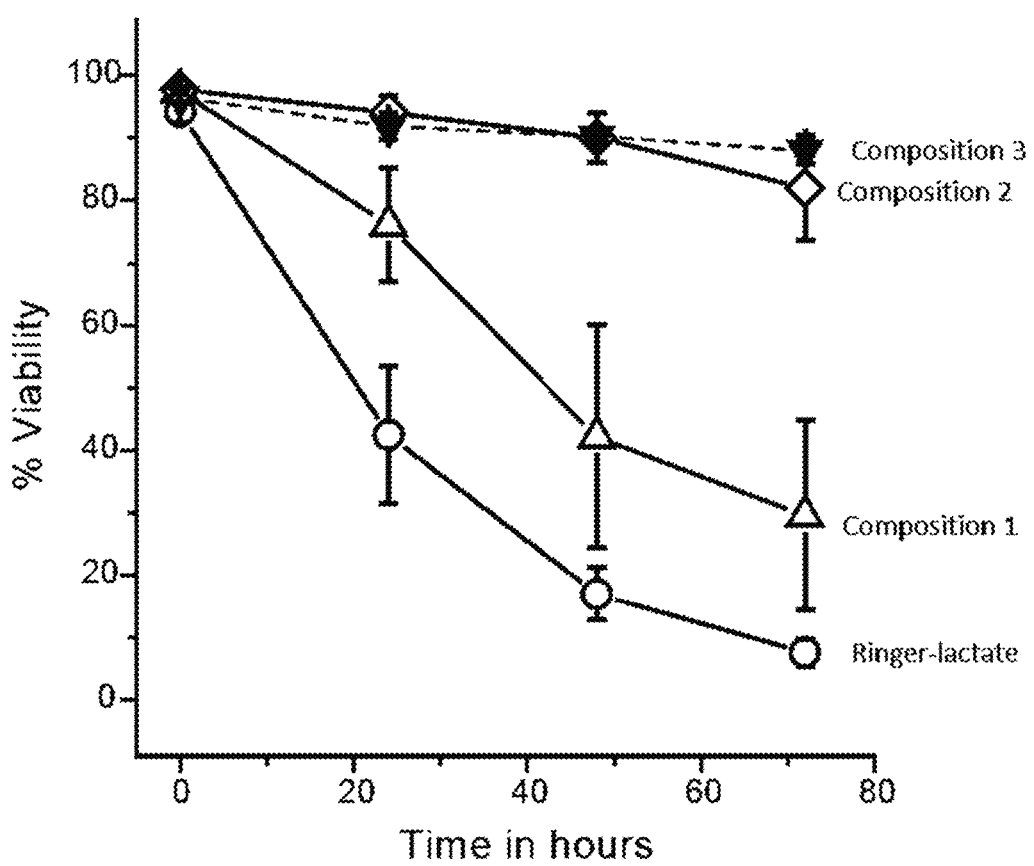
FIG. 2: effects of Composition 2 and Composition 3, according to the invention, and of reference Composition 1 and a composition comprising a Ringer's lactate solution supplemented with glucose and human serum albumin, on cell viability during 3 days storage under hypothermic conditions. (2-8° C.). Data are mean±sem of 5 different donors

FIGS. 1 and 2 show the effects of several compositions on cell viability during 3 days storage under hypothermic conditions. (2-8° C.).

The usual transport solution, Ringer-Lactate supplemented with glucose and Human serum albumin (shown in circles in FIGS. 1 and 2), stabilized the cryopreserved and restored MSCs for 12 hours but it is unsuitable for longer periods.

A combination of SSP+ (Platelet additive solution, Ringwald et al. 2006, Transfusion Med Rev, vol 20, num 2, 158-164) with Ringer Lactate supplemented with glucose and human serum albumin (Composition 1, shown with empty triangles in FIGS. 1 and 2) did not also improve sufficiently the viability of the cells during 3 days storage under hypothermic conditions. (2-8° C.), however, when to that solution trolox is added to obtain composition 2 (shown with diamonds in FIGS. 1 and 2), the stability increases very significantly, as shown in FIGS. 1 and 2, wherein said composition provided more than 80% viability after 72 hours.

Composition 3 with trolox also provided similar performance as seen in FIG. 2 (shown with filled triangles).

Preservation seemed adequate with compositions 2 and 3 even after 7 days at 4° C.

Example 3: Viability and Characterization of a Composition Comprising an Enriched Population of Functional Mesenchymal Stem Cells, Obtained in Example 1

A study of 7 batches originated from seven different donors, of compositions comprising an enriched population of functional MSCs, were prepared with the isotonic medium with trolox, composition 3, according to Example 2, directly after obtaining the cells as described in Example 1, according to the method of present invention, was carried out, and a group of parameters were evaluated, in order to:
  prove that the enriched population of functional mesenchymal stem cells, obtained in Example 1, according to the method of the invention are suitable for application in therapy
  prove that the enriched population of functional mesenchymal stem cells, obtained in Example 1, preserve the typical characteristics of MSCs defined by the Society for Cellular Therapy (ISCT) (Dominici at al., Cryotherapy, 2006, vol 8, No 4, 315-317); (Wuchter et al, Cryotherapy, 2015, 17:128-139), and
  demonstrate the absence of phenotype and genotype aberrations in the enriched population of functional mesenchymal stem cells, obtained in Example 1.

The parameters measured were:
1. cellular morphology measured by adhesion capability;
2. cellular performance measured as expansion (growth) capability of the cells per cm$^2$;
3. cell viability measured using Trypan Blue;
4. immunophenotype analysis analyzing positive expression of CD73, CD90, CD105 and CD166 and negative expression of CD14, CD34, CD45 and HLA-DR;
5. sterility of the compositions obtained according to the method of the invention; and
6. cytogenetic studies to check for structural abnormalities and genetic aberrations.

Morphology: In all the 7 cases assessed, cell cultures presented adherent cells of fibroblastic aspect.

Cellular performance: The number of cells per cm$^2$ obtained is shown in Table 2 for the enriched population of functional mesenchymal stem cells, obtained in Example 1, (Processed MSCs) in Example 1, and of control MSCs (Control MSCs) that have not gone through the method of the invention.

TABLE 2

| DONOR | Performance Control MSCs (cells/cm$^2$) | Performance Processed MSCs (cells/cm$^2$) |
|---|---|---|
| 1 | 18019 | 9707 |
| 2 | 25021 | 18227 |
| 3 | 12228 | 12500 |
| 4 | 22966 | 22138 |
| 5 | 19079 | 15972 |
| 6 | 13349 | 19340 |
| 7 | 18078 | 23758 |
| MEAN ± SEM | 18391 ± 1753 | 17377 ± 1906 |

The mean numbers of cells/cm$^2$, 18391 vs 17377 (last line in Table 2) do not differ significantly, indicating that the method of the invention has not affected the growth of the cells.

Viability: The cell viability obtained, of the enriched population of functional mesenchymal stem cells, obtained in Example 1 (Processed MSCs) and of control MSCs (Control MSCs) that have not gone through the method of the invention, is shown in Table 3:

TABLE 3

| DONOR | VIABILITY MSCs Non-processed (%) | VIABILITY MSCs Processed (%) |
|---|---|---|
| 1 | 99 | 95 |
| 2 | 98 | 96 |
| 3 | 96 | 93 |
| 4 | 99 | 90 |
| 5 | 99 | 98 |
| 6 | 98 | 98 |
| 7 | 99 | 96 |
| MEAN ± SEM | 98.3 ± 0.4 | 95.1 ± 1.2 |

Viability was very much preserved, and no significant differences between the values found in controls and cells obtained in Example 1 (98 vs 95; see last line in Table 3)

In all cases, cell viability must be ≥70%.

Immunophenotypic Analysis:

In 2006, the ISCT proposed three criteria for defining mesenchymal cells: first, these cells must be adherent in culture; second, express CD90 and CD105 antigens in the absence of hematopoietic antigens such as CD34 and CD45; and third, mesenchymal cells must be able to differentiate "In Vitro" into osteoblasts, adipocytes and chondrocytes. In addition, since this population does not present a characteristic phenotype, other adhesion molecules such as the presence of CD73, CD166 and absence of CD14 and HLA-DR should be analyzed.

The phenotypic control of the enriched population of functional mesenchymal stem cells was carried out by means of an analysis of the surface antigens by flow cytometry, which allows us to verify the presence of specific markers of mesenchymal cells.

A suspension of 1 million functional mesenchymal stem cells in 2 ml of PBS was prepared, distributed in 4 tubes (250,000 cells/tube in a volume of 500 µl), and marked with the antibody pattern shown in Table 4 below. The doses used were the recommended by the manufacturer.

Table: Antibody Combination Pattern for Cytometry Analysis

TABLE 4

| 1 | | CONTROL | |
|---|---|---|---|
| 2 | CD 14 | CD 166 | CD 34 |
| 3 | CD 45 | CD 73 | CD 90 |
| 4 | CD 105 | HLA-DR | CD 90 |

The tubes were incubated in the dark at 4° C. for 20 minutes. After this time, 2.5 ml of PBS was added to wash and centrifuged for 5 minutes at 2000 rpm. The supernatant was removed, and the cell pellet resuspended in 500 µl of PBS before passing the sample through the flow cytometer.

The analysis showed that both, the enriched population of functional mesenchymal stem cells, obtained in Example 1, and control MSCs (fresh MSCs) that have not gone through the method of the invention, expressed CD73, CD90, CD105 and CD166 (>90%) and were negative (<10%) for CD14, CD34, CD45 and HLA-DR.

On the other hand, we have studied the percentage of expression of the markers used in the immunophenotypic study (see Table 5) in seven donors.

TABLE 5

| | % EXPRESSION MARKERS | | | | | | | |
|---|---|---|---|---|---|---|---|---|
| | CD14 | CD34 | CD45 | CD37 | CD90 | CD105 | CD166 | HLA-DR |
| 1 | 0.04 | 0 | 0.03 | 100 | 99.97 | 99.67 | 99.96 | 0.77 |
| 2 | 0.23 | 0.17 | 0.07 | 100 | 100 | 97.22 | 99.6 | 0.10 |
| 3 | 0.04 | 2.36 | 0.15 | 99.95 | 99.75 | 97.58 | 99.79 | 2.47 |
| 4 | 0.12 | 0.06 | 0.14 | 99.86 | 99.94 | 96.5 | 99.74 | 0.22 |
| 5 | 0 | 0.03 | 0 | 100 | 99.97 | 99.05 | 100 | 0.39 |
| 6 | 0.17 | 0.11 | 0.19 | 99.94 | 100 | 98.96 | 99.91 | 0.18 |
| 7 | 0.07 | 0.32 | 0.33 | 100 | 99.51 | 92.03 | 100 | 0.08 |

Sterility of the Cells Obtained.

Results obtained in the products sterility assessment are in accordance with the established acceptance criteria. No microbiological growth (detected by $CO_2$ production in an automated system-Bact/Alert and conforming European Pharmacopoeia Monograph 6.2.27) was observed in any case and no presence of mycoplasma was detected. by PCR/NAT based procedure complying European Pharmacopoeia Monograph 6.2.7.

Cytogenetic Studies.

In addition to all the above, the karyotype of the enriched population of functional mesenchymal stem cells, obtained in Example 1, was obtained and evaluated to rule out possible chromosomal aberrations of the medicine.

In the cytogenetic study performed the enriched population of functional mesenchymal stem cells, obtained in Example 1, there were no structural abnormalities verified by G bands (with a resolution of 400 bands).

In summary, from the results obtained in this example we can conclude that:

1. Both, the enriched population of functional mesenchymal stem cells, obtained in Example 1, (Processed MSCs) and control MSCs (Control MSCs) that have not gone through the method of the invention are adherent cells of fibroblastic appearance.

2. The number of cells obtained per $cm^2$ in the enriched population of functional mesenchymal stem cells, obtained in Example 1, is the same as in the control and sufficient to perform quality controls as well as to obtain adequate treatment doses.

3. The viability of both the enriched population of functional mesenchymal stem cells, obtained in Example 1, (Processed MSCs) and control MSCs (Control MSCs), that have not gone through the method of the invention, is the same and above the lower limit fixed (≥70%).

4. The phenotype of both, the enriched population of functional mesenchymal stem cells, obtained in Example 1, (Processed MSCs) and control MSCs (Control MSCs), that have not gone through the method of the invention, meet the criteria established by the International Society for Cellular Therapy (ISCT): expression of CD105 and CD90, in the absence of typically hematopoietic markers such as CD34, CD45 and HLA-DR. The cells (both, control and processed) are also positive for CD73, CD166 and do not express CD14. Taking into account the expression percentages obtained, and following the parameters settled in ISCT (Wuchter et al, 2015), we established the acceptance criterion in the expression ≥90% for considered positive markers like CD73, CD90, CD105 and CD166, and the expression ≤10% is considered negative for markers like CD14, CD34, CD45 and HLA-DR.

5. In summary, the method of the invention does not modify or transform the characteristics of the enriched population of functional MSCs obtained by said method, thus being bioequivalent to MSCs which have not gone through the method of the invention, the fresh cells used before, which showed significant therapeutic value in several indications (Orozco, Transplantation, 2011, 92:822-828; Orozco, Transplantation, 2013, 95(12):1535-1541; Vega, Transplantation 2015, 99:1681-1690; Noriega, Transplantation 2017, 101: 1945-1951).

6. The enriched population of functional mesenchymal stem cells, obtained in Example 1, do not present genotypic aberrations after the cryopreservation process.

7. The absence of chromosomal aberrations in the enriched population of functional mesenchymal stem cells, obtained in Example 1, allow us to conclude that the MSCs remain stable when they undergo up to 10 duplications.

Example 4: Characterization of a Composition Comprising an Enriched Population of Functional Mesenchymal Stem Cells, Obtained According to the Method of the Invention after a 72 Hours-Transport The objectives of test were:

Evaluate the sterility, viability and immunophenotype of the compositions comprising an enriched population of functional mesenchymal stem cells, obtained according to the method of the invention after a 72-hour transport process.

Show that MSCs of said compositions maintain in vitro re-expansion capacity, i.e. the same in vitro growth capability, after carrying out a 72-hour transport process.

As a cellular source of obtaining MSCs processed according to the method of the invention, a bone marrow aspirate from 3 different donors was used and subjected to the protocol anticoagulant procedure. The aspirate sample was processed within 24 hours after its extraction.

The compositions comprising an enriched population of functional MSCs were obtained according to the method of the invention as described in Example 1. The enriched population of functional MSCs obtained were suspended in composition 3 according to the example 3 above herein, and the packaging process was carried out in a 5 ml syringe in doses of 20±2 million cells resuspended in 2 ml for use in degenerative disc disease (DDD) treatments. For use in osteoarthritis the dose of cells would be 40 million cells suspended in 8 ml.

The composition, comprising an enriched population of functional mesenchymal stem cells, obtained according to the method of the invention, has a characteristic immunophenotype of mesenchymal cells, with the presence of CD90, CD105, CD166 and CD73 antibodies, and absence of CD14, CD34, CD45, HLA-DR markers.

Cell viability needs to be greater than 90% for releasing for medical use the obtained compositions and, the viability of the released compositions must be greater than 80% within 72 hours of its issue (product expiration date) after performing a shipping simulation, since this product has a stability of 72 hours at 2-8° C.

The dose for therapy was 20±2×10$^6$ cells in a final volume of 2 ml. The container containing the composition was identified by a label containing the data of the manufactured product.

The composition was transported in an ORCA equipment which is a validated isothermal packaging that ensures a constant temperature between 2 and 8° C. for at least 168 hours, at all times of the year and climatic conditions. In addition, the packaging does not require transportation in refrigerated vehicles. Also, each box incorporated a data logger (thermo-recorder) that provided a graph of the temperature at which the product had been maintained throughout the transport time.

The ORCA® packaging which consists of a box of 4.4 L with external dimensions 345×317×308 mm and a weight of 7.2 kg.

To demonstrate that the compositions obtained in this example suspended with composition 3, according to present invention, remain stable after the 72-h transport process and maintains sterility, viability and phenotypic characteristics of MSCs defined by the Society for Cellular Therapy (ISCT) (Dominici et al., Cryotherapy, 2006, vol 9, No 4, 315-317), a study of 3 lots was carried out to evaluate the following parameters:

Transport temperature
Cell Viability
Immunophenotypic analysis
Sterility
Growth kinetics test to verify that cells maintain the ability to duplicate after the transport process.

The ORCA isothermic packaging allowed the transport temperature to be maintained for 72 hours in a range of 2 to 8° C.

Cell Viability

Cell viability was evaluated at 72 h after the transport process, with the Trypan Blue exclusion method. All trials were performed in triplicate. Table 6 shows the initial viability of the donors analyzed and the mean viability obtained at 72 hours±standard deviation.

TABLE 6

| DONOR | % Viability Initial | % Viability 72 hour |
|---|---|---|
| 1 | 99 | 83.9 ± 2.9 |
| 2 | 98.4 | 84.2 ± 2.3 |
| 3 | 97 | 84.5 ± 2.4 |

In all cases, the cellular viability at 72 hours was ≥80%, so it meets the criteria established in this study.

Immunophenotypic Analysis

Flow cytometry analysis showed that at 72 hours after the compositions were dispatched, the cells tested expressed CD73, CD90, CD105 and CD166 and were negative for CD14, CD34, CD45 and HLA-DR in all composition's expression pattern. Table 5 shows the percentage of expression of the markers analysed by flow cytometry at the time of shipment of the compositions and at 72 hours after the product was shipped. All donors show a mesenchymal cell phenotype after the transport process.

TABLE 7

| | DONOR 1 | | DONOR 2 | | DONOR 3 | |
|---|---|---|---|---|---|---|
| MARKERS | INITIAL | 72 HOUR | INITIAL | 72 HOUR | INITIAL | 72 HOUR |
| CD14 | 0 | 0 | 0.4 | 0.1 | 0.1 | 0 |
| CD34 | 0.1 | 0.1 | 2.5 | 0 | 0 | 0 |
| CD45 | 0 | 0 | 0.6 | 0.1 | 0.1 | 0 |
| CD73 | 99.7 | 100 | 99.8 | 99.9 | 100 | 99.8 |
| CD90 | 99.8 | 100 | 99.8 | 99.3 | 99.9 | 99.9 |
| CD105 | 93.9 | 99.7 | 93.9 | 96.6 | 98.6 | 98.5 |
| CD166 | 99.8 | 99.8 | 99.8 | 99 | 99.9 | 99.9 |
| HLA-DR | 1.3 | 0.1 | 1.3 | 0 | 0 | 0.1 |

Growth Kinetics Test

Growth kinetics tests we carried out recording the number of cells at different time intervals when culturing after the transport process. These results show that in for the three donors analysed, the enriched population of functional MSCs maintain the capacity of duplication after a transport process of 72 hours.

Sterility

The sterility of the compositions was evaluated after the simulation of the transport. After 72 hours of obtaining the composition with the enriched population of functional mesenchymal stem cells, 3 cell expansion processes were initiated. These expansions were maintained for a period of 11 days with culture media without antibiotics. None of the three cultures shows signs of microbiological contamination, all present adequate growth kinetics and therefore maintain sterility.

Based on the results obtained in this study, we can conclude that:
1. The viability of the mesenchymal cells in the compositions obtained with the method of the invention after a 72 hours transport process was ≥80%.
2. In the study of growth kinetics, it is observed that the mesenchymal cells comprised in the compositions, maintained in culture medium without antibiotic, preserve the sterility after transport.
3. The phenotype of the mesenchymal cells comprised in the compositions following a 72-hour transport process complies with the criteria established by the International Society for Cellular Therapy (ISCT): expression of CD105 and CD90, in the absence of typically hematopoietic markers such as CD34, CD45 and HLA-DR. They are also positive for CD73, CD166 and do not express CD14. With percentages of expression ≥90% for the positive markers and ≤10% for the negative markers.
4. The mesenchymal cells comprised in the compositions maintain the "in vitro" reexpansion capacity after carrying out a hypothermic transport process of 72 hours, since they are able to divide.

Example 5: Reproducibility of the Method

The present example aims to verify the reproducibility of the process, to evaluate if said process provides a standardized product adequate for use in therapy as a medicinal product, and to confirm that the product obtained complies with a set of final product specifications. Bone marrow aspirates were the cellular source for obtaining the compositions of the invention used in the test, processed according to the donation requirements according set by Directive 2006/17/EC and Spanish RD1301/2006.

The bone marrow aspirates were processed within 24 hours after extraction.

The yield and viability of mononuclear cells in the samples are shown in table 8:

TABLE 8

|  | Mononuclear cells | |
| --- | --- | --- |
|  | COUNTING | VIABILITY |
| DONOR 1 | 360,400,000 | 99% |
| DONOR 2 | 1,350,719,900 | 99% |

The isolation of samples of mesenchymal stem cells, to be used in the method of the invention, takes approximately 21 to 28 days, as detailed above. A fraction of mononuclear cells (MNCs) was selected in said samples by density gradient method with Ficoll. At the end of this process, counting and viability controls were performed using the Trypan Blue exclusion method with Neubauer Chamber. At this point, the mononuclear cells with a viability greater than 70% were selected to start the process of obtaining mesenchymal cells.

After the selection process, MNCs were seeded at a density of 175,000 cells/cm$^2$ and kept in culture at 37° C. and 10% $CO_2$. Every 3 or 4 days, the appearance of the cell was observed with inverted microscope, and the percentage of growth was recorded. If it was less than 60-80% a change of medium was made, and if it was greater than 80%, dissociation and cellular expansion (pass) was carried out, performing subcultures in order to increase and purify the MSCs over other non-dividing cells present in the sample.

An immunophenotypic study was performed by flow cytometry and showed that the mesenchymal cells in the sample expressed CD73, CD90, CD105 and CD166 in a percentage ≥90% and were negative for CD14, CD34, CD45 and HLA-DR markers, since their expression was ≤10%

Table 9 shows the percentage of expression of the markers analysed by flow cytometry at the time of obtaining the cellular stock of the two analysed donors:

TABLE 9

| MARKERS | Expression | DONOR 1 | DONOR 2 |
| --- | --- | --- | --- |
| CD14 | ≤10% | 0.07% | 0% |
| CD34 | ≤10% | 0.04% | 0.05% |
| CD45 | ≤10% | 0% | 0.04% |
| CD73 | ≥90% | 100% | 98.53% |
| CD90 | ≥90% | 99.92% | 99.33% |
| CD105 | ≥90% | 99.73% | 91.08% |
| CD166 | ≥90% | 98.21% | 99.19% |
| HLA-DR | ≤10% | 0.04% | 0.05% |

Cells obtained during this first step were cryopreserved for obtaining the mesenchymal stem cell sample of step (a) of the method of the invention.

At this point, an enzymatic digestion with tripsin-EDTA was performed thus allowing to obtain a cell suspension which is cryopreserved in FBS containing 10% DMSO or with commercial kits (CryoStor® CS5) and stored in liquid nitrogen at −196° C. for 24 days.

The process of restoration and revitalization lasts approximately 7 to 10 days, allowing to obtain the compositions containing MSCs according to the invention.

The restoration process begins by thawing a cryovial incubated 1-2 min at 37° C. or using automatized devices such as a ThawSTAR® CFT2 Thawing Instrument, and the cells were seeded at a density of 2,000 cells/cm$^2$.

Controls performed after the thawing of the samples showed satisfactory results as seen in Table 10, in terms of viability and cell counting and, therefore the cellular restoration process was started to obtain the compositions of the invention.

TABLE 10

| QCs on Product after freezing | DONOR 1 | DONOR 2 |
| --- | --- | --- |
| Vial integrity | Entire and sealed | Entire and sealed |
| Viability | 78.6% | 86% |
| Cell-Counting | 8,000,000 cells | 7,068,666 cells |
| Sterility | Sterile | Sterile |

The culture was maintained at 37±2° C. and 10% $CO_2$. Every 3-4 days a medium change was performed. During this process, the culture was monitored with the inverted microscope and it was verified that the mesenchymal cells preserve their fibroblastic morphology after the cryopreservation and thawing process.

When the culture reached 80% of confluency, the mesenchymal stem cells were recovered by enzymatic dissociation with trypsin-EDTA.

The enriched population of functional mesenchymal stem cells recovered were then resuspended in the composition 3 of example 2, and the packaging process was carried out in a 5 ml syringe in doses of 20±2 million cells resuspended in 2 ml.

The enriched population of functional mesenchymal cells were analysed by cytogenetic studies to verify if they presented alterations at karyotype level after the cryopreservation and thawing process. Results obtained from this analysis do not show chromosomal aberrations. The results of the controls performed are shown in Table 11:

TABLE 11

| Active Substance QCs | DONOR 1 | DONOR 2 |
| --- | --- | --- |
| Mycoplasma Detection | Absence | Absence |
| Viability | 93% | 97% |
| Cell-counting | 23,077,500 cells | 24,897,500 cells |
| Sterility | Sterile | Sterile |
| Karyotype | No chromosomic aberrations | No chromosomic aberrations |
| Cumulative population doublings (PD) | 1.86 | 1.97 |
| Immunophenotype | Complying | Complying |

The immunophenotypic study performed by flow cytometry on the active substance shows that the enriched population of functional mesenchymal cells of the compositions obtained expressed CD73, CD90, CD105 and CD166 in a percentage ≥90% and were negative for CD14, CD34, CD45 and HLA-DR, since its expression was ≤10%. Table 12 shows the expression percentage of the markers analysed by flow cytometry at the time of obtaining the active substance from the two donors analysed:

TABLE 12

| MARKERS | Expression | DONOR 1 | DONOR 2 |
| --- | --- | --- | --- |
| CD14 | ≤10% | 0.04% | 0% |
| CD34 | ≤10% | 0% | 0% |
| CD45 | ≤10% | 0.36% | 0.04% |
| CD73 | ≥90% | 99.28% | 97.75% |
| CD90 | ≥90% | 98.25% | 99.67% |
| CD105 | ≥90% | 97.99% | 98.75% |
| CD166 | ≥90% | 100% | 100% |
| HLA-DR | ≤10% | 0.09% | 0.14% |

In addition, in the study of the potency performed it is observed that the cells differentiate to chondrogenic tissue. They were kept in culture for 30 days with conditioned medium and the histological study was carried out by staining with Alcian Blue that allows us to observe the acidic polysaccharides found in differentiated cells towards cartilage. The results of the controls performed on the final product are shown in table 13.

TABLE 13

| QCs on Final Product | DONOR 1 | DONOR 2 |
| --- | --- | --- |
| Cell concentration | 10,000,000/1 ml | 10,000,000/1 ml |
| Viability | 93% | 97% |
| Sterility | Sterile | Sterile |
| Appearance on integrity | Withish cell suspension | |

The compositions obtained, containing an enriched population of functional mesenchymal stem cells obtained according to the method of the invention, contained 20 million±2 million cells resuspended in composition 3 according to Example 2.

In this case, the packaging of 10 million in 1 ml was chosen since it is the density established for the treatment of disc regeneration. Those compositions were packed in a 5 ml syringe containing 2 ml of cell suspension, with a stability of 72 hours at 2-8° C.

The container carrying the compositions of the invention was identified with a label including the data of the product. This container was then introduced into a sterile bag and exited the sterile zone to the conditioning area, where the secondary packaging is performed in a box with the corresponding identification.

The compositions were transported in a validated isothermal package which ensured a temperature maintained between 2 and 8° C. for up to 168 hours, also containing a data logger that provides a graph of the product temperature throughout all the transport process.

In addition, during the whole manufacturing process, it is ensured the aseptic manufacture of the compositions.

Example 6: Evaluation of Cell Viability

To compare the cell viability profile of the mesenchymal stem cells included in the compositions obtained according to the method of the invention, with current cryopreservation methods.

To this end, a first sample of mesenchymal stem cells was cryopreserved with 10% DMSO and FBS, restored at 35-39° C. with DMEM with 10% $CO_2$, and transport conditioned to obtain composition 3 according to the method of the invention.

A second sample of mesenchymal stem cells was frozen in Hypothermosol® FRS (containing no DMSO!) and thawed at room temperature (21-25° C.).

A third sample of mesenchymal stem cells was frozen in saline medium containing 10% DMSO and thawed at room temperature (21-25° C.).

Values are means+/−SD of 3 donors. All the measurements were done by in triplicate.

Figure 3:
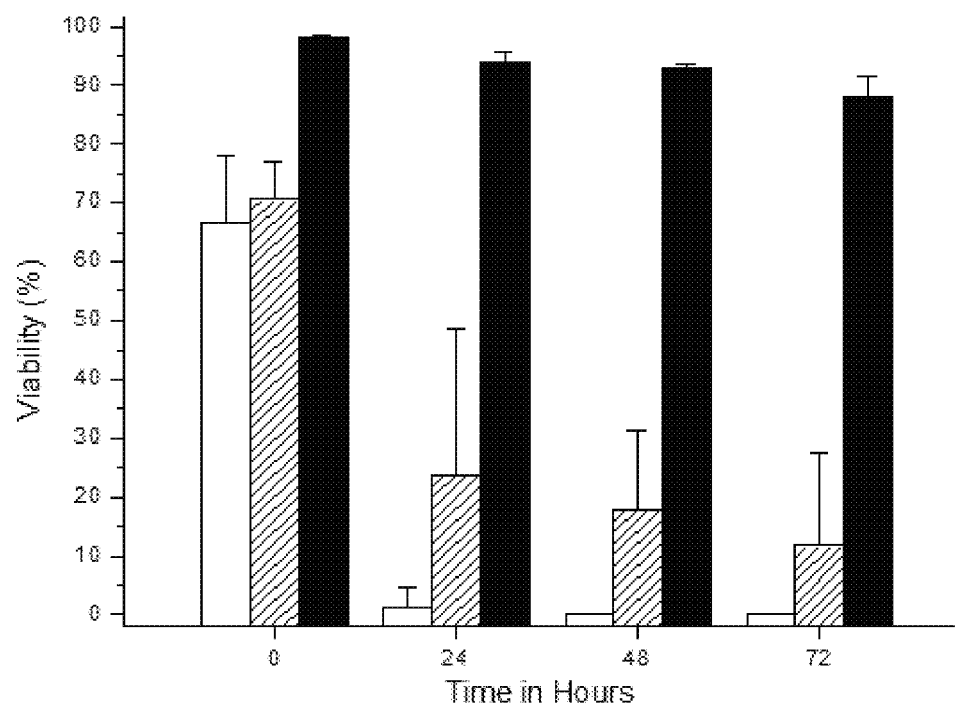
FIG. 3: Cell viability versus time achieved by (1) the compositions comprising MSCs cryopreserved in FBS+10% DMSO, restored at 35-39° C. with medium comprising 10% $CO_2$ and transport conditioned to obtain composition 3, according to the invention (filled bars); (2) with a composition comprising MSCs in Hypothermosol® with trolox cryopreserved and thawed and maintained at room temperature (20-25° C.) for the times indicated, according to WO2010/064054 (bars with diagonal lines); and (3) with a composition comprising MSCs in Ringer Lactate and 10% DMSO cryopreserved and thawed (white bars). Values are means+/−SD of 3 donors. All the measurements were done by in triplicate.

As seen in FIG. 3, the mesenchymal stem cells included in the compositions obtained according to the method of the invention provided a viability above 80% even after 72 hours of storage (black bars). On the other hand, mesenchymal stem cells cryopreserved in Hypothermosol® FRS, without DMSO and thawed at room temperature (bars with diagonal lines), provided lower than 50% viability after only 24 hours of storage. The viability results of cells cryopreserved with DMSO in saline and directly thawed without restoration according to the invention step were even lower. Only the compositions obtained according to the invention showed an adequate stability and viability for postponed therapeutic use.

Reference Example 7: Evaluation of Cell Growth Profile of Fresh Mesenchymal Stem Cells in the Presence of DMSO The cell growth profile of the mesenchymal stem cells in presence of DMSO was analysed to evaluate the effect of DMSO in current cryopreservation methods, which make use of the cells directly after thaw and may be contaminated with DMSO.

For this purpose, a sample of freshly prepared MSCs was grown in DMEM containing FBS, 10% $CO_2$ and different concentrations of DMSO, as shown.

Figure 4:
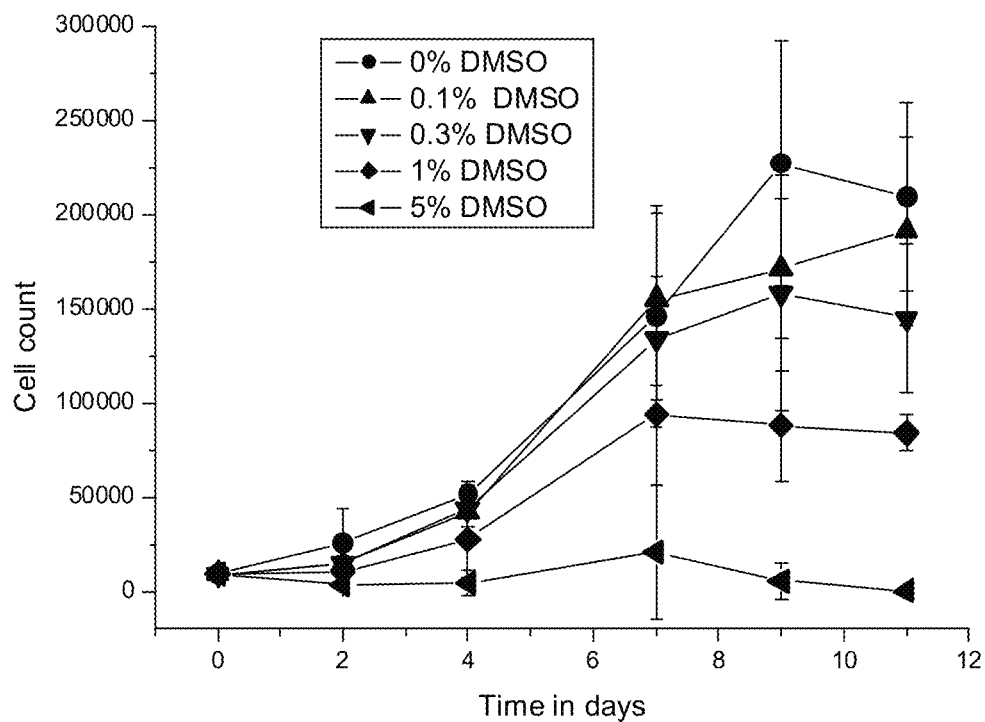
FIG. 4: Effect of DMSO in mesenchymal stem cells growth. Fresh mesenchymal stem cells were seeded at 1000 cells per $cm^2$ with 0%, 0.1%, 0.3%, 1% and 5% DMSO and grown at 37° C. for the times shown. The values are mean±SD of 3 donors.

Reference FIG. 4 shows that DMSO interferes significantly with growth at concentrations as low as 0.3%, suggesting that even a small contamination with DMSO, such as the produced during use in the freezing-thawing steps, may hinder growth.

Example 8: Evaluation of the Cell Growth Profile

Cell growth was also evaluated for a composition comprising functional cryopreserved, restored and transport conditioned mesenchymal stem cells obtained according to the method of the invention after thawing, restoration and 72 hours transport at 4° C. (CRT).

To this end, a sample of mesenchymal stem cells was cryopreserved with 10% DMSO and FBS, restored at 35-39° C. with DMEM with 10% $CO_2$ for 7 days, transport conditioned to obtain composition 3 according to the method of the invention and incubated in hypothermia (2-8° C.) during 72 hours and subsequently cultured as in FIG. 4.

Figure 5:
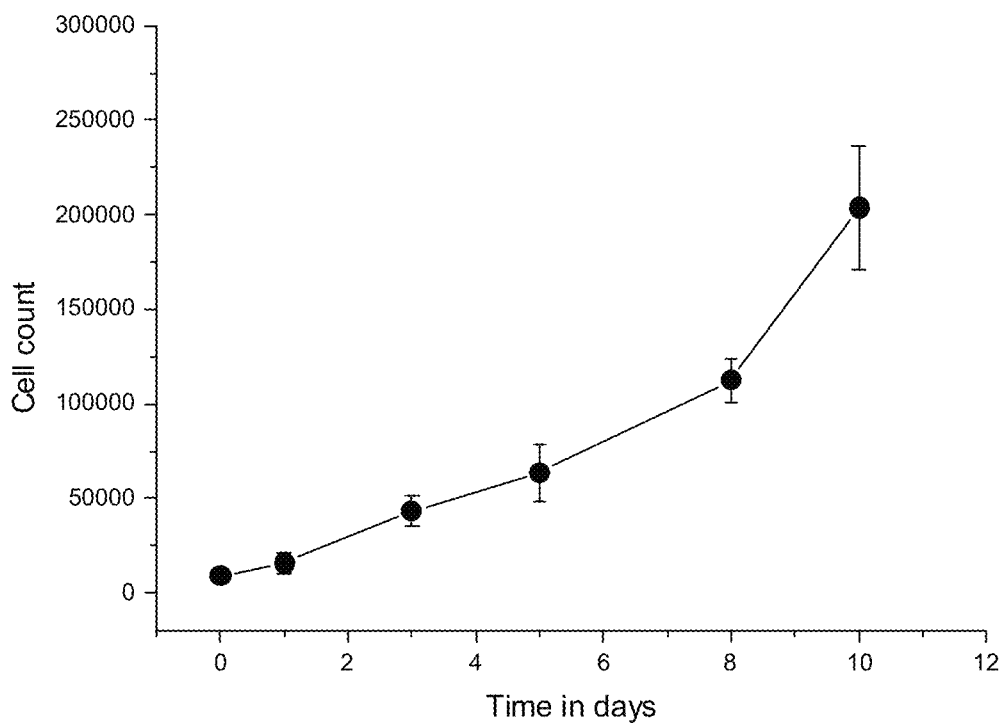
FIG. 5: growth curve of composition 3 comprising cryopreserved, restored and transport conditioned mesenchymal stem cells obtained according to the method of the invention after 72 hours of hypothermic transport (2-8° C.). Mean±SD of triplicate values. Representative of 3 similar experiments with different donors.

FIG. 5 shows how the growth profile of the mesenchymal stem cells included in the compositions obtained in the method of the invention is similar to that of cells cultured without DMSO (FIG. 4). This means that the process of restoration described here eliminates any of the possible interactions and toxicity found in the use of DMSO during cryopreservation, while providing a significantly improved cell viability profile even after 72 hr of hypothermic storage following restoration and conditioning in the transport solution, according to the method of the invention.

The stability, viability and cell growth profile of the compositions obtained according to the method of the invention allow their storage and postponed use in therapy and solve the issues of DMSO toxicity when administered. The method of the invention also allows to obtain mesenchymal stem cells with suitable phenotype, cell grow and viability profile, in sufficient number for therapeutic doses, solving the issues described in the prior art. Optimal results require not only the adequate compositions in each one of the steps described, Cryopreservation, Restoration and Transport-conditioning procedures, but adequate sequence and duration of each elementary step.

The invention claimed is:

1. A method for obtaining a composition comprising functional mesenchymal stem cells that have been cryopreserved, restored, and conditioned for transport and storage and are suitable for administration in therapy, said method comprising the steps of:
   a. suspending an ex vivo sample of bone marrow mesenchymal stem cells in a cryoprotecting medium comprising 5% to 10% dimethyl sulfoxide at a concentration of $5 \times 10^6$ to $10 \times 10^6$ cells/ml;
   b. cryopreserving the sample of bone marrow mesenchymal stem cells, cooling them first from −70° C. to −90° C. for at least 24 hours prior to storing the sample in liquid nitrogen;
   c. restoring the sample of bone marrow mesenchymal stem cells, by performing the following steps:
      c1. thawing the sample of the bone marrow mesenchymal stem cells by progressively increasing the temperature up to 35-39° C. during 1 to 5 minutes;
      c2. diluting a volume of the thawed sample from c1 10 to 30 times with suitable culture medium;
      c3. centrifuging the diluted sample from c2, discarding the supernatant and resuspending the pellet of mesenchymal stem cells in suitable culture medium;
      c4. selecting the mesenchymal stem cells with a viability of at least 70%;
      c5. seeding the mesenchymal stem cells selected in step (c4) on a plastic support and incubating said mesenchymal stem cells with a suitable culture medium comprising 7.5% to 10% $CO_2$ and at least 5% fetal bovine serum at a cell concentration between 1000 to 5000 cells/cm², with adequate culture conditions at 35-39° C.,
      c6. replacing with fresh suitable culture medium comprising 7.5% to 10% $CO_2$ and at least 5% fetal bovine serum maintained at 35-39° C., at regular time intervals and isolating the mesenchymal stem cells from the support when the cells occupy 80 to 100% of the support's surface;
      c7. selecting the mesenchymal stem cells that:
         show adherence to plastic; and
         present a viability of at least 70%; and
         present an expression ≥90% of CD90, CD 166, CD73 and CD105; and
         present an expression ≤10% of CD14, CD34, CD45 and HLA-DR≤10%; and
         do not feature chromosomal aberrations; and
         present capacity to differentiate into osteoblasts, adipocytes and chondrocytes; and
   d. conditioning the mesenchymal stem cells isolated in step (c7) for transport and storage at 2-8° C. by suspending the restored mesenchymal stem cells in an isotonic medium, wherein the conditioned mesenchymal stem cells have a viability of at least 70% at 2-8° C. for at least 72 hours, wherein said isotonic medium comprises 6-hydroxy-2,5,7,8-tetramethylchroman-2-carboxylic acid 0.25 to 1 mM.

2. The method according to claim 1, wherein the cryoprotecting medium of step (a) comprises fetal bovine serum and 5% to 10% DMSO.

3. The method according to claim 1, wherein the cryoprotecting medium of step (a) is an animal component-free, serum-free and protein-free medium, comprising 5% or 10% DMSO.

4. The method according to claim 1, wherein step (b) comprises cryopreserving the sample of bone marrow mesenchymal stem cells at a speed of 1° C./min from −70° C. to −90° C. for at least 25 hours prior to storing the sample in liquid nitrogen.

5. The method according to claim 1, wherein the isotonic medium comprising 6-hydroxy-2,5,7,8-tetramethylchroman-2-carboxylic acid 0.25 mM to 1 mM, is an animal component-free serum-free protein-free medium.

6. The method according to claim 1, wherein the isotonic medium comprising 6-hydroxy-2,5,7,8-tetramethylchroman-2-carboxylic acid 0.25 mM to 1 mM comprises a 1:9 to 9:1 mixture (v/v) of a first composition comprising $Na^+$ 130 mM, $K^+$ 4 mM, $Ca^{2+}$ 1.35 mM, Chloride 109 mM and lactate 16 mM, with a second composition comprising $Na^+$ 159 mM, $K^+$ 5 mM, $Mg^{2+}$ 0.8 mM, Chloride 77 mM, dihydrogen phosphate 28 mM, citrate 10 mM and acetate 32 mM, supplemented with glucose 5 mM, and human serum albumin 0.1% to 0.5%.

7. A composition comprising a population of at least $0.5 \times 10^6$ mesenchymal stem cells and 6-hydroxy-2,5,7,8-tetramethylchroman-2-carboxylic acid 0.25 mM to 1 mM obtainable according to the method of claim 1, wherein said mesenchymal stem cells retain for at least 72 hours during hypothermic transport at 2-8° C., the characteristics of fresh mesenchymal stem cells, including:
   showing adherence to plastic;
   presenting a viability of at least 70%;
   presenting an expression ≥90% of CD90, CD 166, CD73 and CD105;
   presenting an expression ≤10% of CD14, CD34, CD45 and HLA-DR≤10%;
   not featuring chromosomal aberrations; and
   presenting capacity to differentiate into osteoblasts, adipocytes and chondrocytes.

8. A method of treating an osteoarticular disease, an autoimmune disease or a cardiovascular disease, comprising administering a therapeutic amount of the composition according to claim 7 to a subject in need thereof.

9. The method according to claim 8, wherein said composition is administered at a cell density of $1\times10^6$ to $10\times10^6$ cells/ml and at 0.5 to 90 million cells.

10. The method according to claim 8, wherein the osteoarticular diseases are selected from the group consisting of degenerative disc disease, osteoarthritis, meniscus injuries, and rheumatoid arthritis.

11. The method according to claim 8, wherein the autoimmune diseases are selected from the group consisting of lupus erythematosus, graft-versus-host disease, and systemic sclerosis.

12. The method according to claim 8, wherein the cardiovascular diseases are selected from the group consisting of peripheral vascular insufficiency, myocardial infarction, stroke, and ischemia.

13. The method according to claim 8, wherein the treatment is autologous or allogenic.

14. The method according to claim 1, wherein the bone marrow mesenchymal stem cells are of human origin.

\* \* \* \* \*